(12) United States Patent
Tanaka et al.

(10) Patent No.: US 9,975,910 B2
(45) Date of Patent: May 22, 2018

(54) HETERO-FUSED CYCLIC COMPOUND

(71) Applicant: Eisai R&D Management Co., Ltd., Tokyo (JP)

(72) Inventors: Keigo Tanaka, Tsukuba (JP); Takashi Fukuyama, Tsukuba (JP); Norio Murai, Tsukuba (JP); Wataru Itano, Tsukuba (JP); Shinsuke Hirota, Tsukuba (JP); Daisuke Iida, Tsukuba (JP); Hiroshi Azuma, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days. days.

(21) Appl. No.: 14/904,860

(22) PCT Filed: Jul. 18, 2014

(86) PCT No.: PCT/JP2014/069153
§ 371 (c)(1),
(2) Date: Jan. 13, 2016

(87) PCT Pub. No.: WO2015/012210
PCT Pub. Date: Jan. 29, 2015

(65) Prior Publication Data
US 2016/0168176 A1 Jun. 16, 2016

(30) Foreign Application Priority Data
Jul. 23, 2013 (JP) .................................. 2013-152677

(51) Int. Cl.
| | | |
|---|---|---|
| C07D 491/048 | (2006.01) | |
| C07F 7/22 | (2006.01) | |
| C07D 493/04 | (2006.01) | |
| C07D 495/04 | (2006.01) | |
| C07D 513/04 | (2006.01) | |
| C07F 5/02 | (2006.01) | |

(52) U.S. Cl.
CPC ........ C07F 7/2212 (2013.01); C07D 491/048 (2013.01); C07D 493/04 (2013.01); C07D 495/04 (2013.01); C07D 513/04 (2013.01); C07F 5/02 (2013.01); C07F 5/025 (2013.01); C07F 5/027 (2013.01)

(58) Field of Classification Search
CPC .................................................. C07D 307/87
See application file for complete search history.

(56) References Cited

U.S. PATENT DOCUMENTS

| | | | |
|---|---|---|---|
| 5,252,538 A | 10/1993 | Cross et al. | |
| 6,444,617 B1 * | 9/2002 | Takaishi | A01N 43/42 504/246 |
| 2006/0217562 A1 | 9/2006 | Semple et al. | |
| 2007/0105943 A1 | 5/2007 | Nakamoto et al. | |
| 2008/0064699 A1 | 3/2008 | Florjancic et al. | |
| 2010/0056788 A1 | 3/2010 | Tanaka et al. | |
| 2010/0137282 A1 | 6/2010 | Davies et al. | |
| 2014/0142085 A1 | 5/2014 | Bondy et al. | |

FOREIGN PATENT DOCUMENTS

| | | |
|---|---|---|
| EP | 2 062 901 | 5/2009 |
| JP | 2007-509181 | 4/2007 |
| JP | 2009-538933 | 11/2009 |
| JP | 2010-155827 | 7/2010 |
| JP | 2010-524884 | 7/2010 |
| WO | WO 1996/005177 | 2/1996 |
| WO | WO 2005/033079 | 4/2005 |
| WO | WO 2006/124324 | 11/2006 |
| WO | WO 2008/032702 | 3/2008 |
| WO | WO 2008/128942 | 10/2008 |
| WO | WO 2013/006738 | 1/2013 |

OTHER PUBLICATIONS

D'souza et al., Iron-Catalyzed Cycloaddition of Alkynenitriles and AlkynesOrganic Letters (2011), 13(11), 2936-2939.*
Buysens et al., Tetrahedron (1995), 51(45), 12463-78.*
Panda et al. Tetrahedron Letters 49 (2008) 6701-6703.*
Young et al., Angewandte Chemie, International Edition (2007),46(27), 5187-5190 CODEN: ACIEF5; ISSN: 1433-7851.*
European Search Report in European Application No. 14829168.5 dated Dec. 2, 2016, 8 pages.
Agarwal et al., "Dihydropyrido[2,3-d]pyrimidines as a new class of antileishmanial agents," Bioorg Med Chem 13(24):6678-6684, Dec. 2005.
Curatolo "Physical chemical properties of oral drug candidates in the discovery and exploratory development settings," Pharm Sci & Tech Today 1(9):387-393, Dec. 1998.
Database Regisrty, RN 1464091-43-7, Retrieved from STN international [online], Oct. 25, 2013, 1 page.
Gharbaoui et al., "Agonist lead identification for the high affinity niacin receptor GPR109a," Bioorg Med Chem Lett 17(17):4914-4919, Sep. 2007.
International Preliminary Report on Patentability in Application No. PCT/JP2014/069153, dated Feb. 4, 2016, 10 pages.
International Search Report in Application No. PCT/JP2014/069153, dated Sep. 22, 2014, 3 pages.
Johnstone et al., "Porphyrin building blocks: using a modified Barton-Zard approach to construct annulated pyrroles," J Porphyrins and Phthalocyanines, 6(11-12):661-672, 2002.

(Continued)

*Primary Examiner* — Paul V Ward
(74) *Attorney, Agent, or Firm* — Fish & Richardson P.C.

(57) ABSTRACT

A compound represented by the formula (I) or a salt thereof:

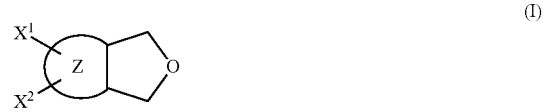

(I)

wherein a ring Z is a 5 to 6-membered heteroaromatic ring having one or two heteroatoms in the ring; $X^1$ is a hydrogen atom, a hydroxy group, a hydroxy $C_{1-6}$ alkyl group, —$B(OH)_2$, a boronate ester group, a cyclic boronate ester group, a boranyl group, a cyclic boranyl group, —$BF_3M_{n1}$, —$Sn(R^{12})(R^{13})(R^{14})$, a leaving group, a carboxy group, a formyl group, or —$NR^{16}R^{17}$; and $X^2$ is a hydrogen atom or —$CO_2R^{18}$.

7 Claims, No Drawings

(56) References Cited

OTHER PUBLICATIONS

Moursounidis and Wege, "The synthesis of thieno[3,4-b]furan using a tandem intramolecular-reverse Diels-Alder reaction approach," Tetrahedron Letters 27(26):3045-3048, 1986.
Parnell and Volhardt et al., "The cobalt way to vitamin B6, Regioselective construction of the tetrasubstituted pyridine nucleus by cobalt-catalyzed alkyne-nitrile cooligomerizations," Tetrahedron (24):5791-5796, 1985.
Robba and Zaluski, "Study of the Catalytic Reduction of Furo[3,4-d]Pyridazines," French Acad Sci 263:429-431, Aug. 1, 1966, including English translation.
Salonen et al., "Identification of detomidine carboxylic acid as the major urinary metabolite of detomidine in the horse," European Journal of Drug Metabolism and Pharmacokinetics, 17(1):13-20, Jan. 1992.
Spinner and Yeoh, "Pyridone-pyridol tautomerism in 2-hydroxypyridines with [5,6]-annelated rings and carbon atoms at positions [5] and [6] : 1,3-dihydro-5-hydroxyfuro[3,4-b]pyridine, 1,3-dihydro-5-hydroxythieno[3,4-b]pyridine, and 1,3-dihydro-5-hydroxythieno[3,4-b]pyridine S,S-dioxide," J Chem Society B: Physical Organic 289-296, 1971.
Wang et al., "Liquid chromatography-mass spectrometry method for determination of tetramethylpyrazine and its metabolite in dog plasma," J of Chroma B 813(1-2):263-268, Dec. 2004.
Yunpeng et al., "Studies on the Metabolites of Tetramethylpyrazine in Human Urine," Acta Academiae Medicinae Sinicae 18(4):288-291, 1996, including English abstract.
Submission Document in European Patent Application No. 14829168.5, dated May 15, 2017, 21 pages.
Office Action in European Patent Application No. 14829168.5, dated Feb. 9, 2018, 5 pages.

\* cited by examiner

HETERO-FUSED CYCLIC COMPOUND

TECHNICAL FIELD

The present invention relates to hetero-fused cyclic compounds.

BACKGROUND ART

Compounds having ortho-dimethyl heteroaromatic rings have been used in drug discovery/research, such as a drug for stroke, tetramethylpyrazine (Patent Literature 1) and a drug for ulcers, revaprazan (Patent Literatures 1 and 2).

However, two things are possibly concealed in use of those compounds having ortho-dimethyl heteroaromatic rings in research for development of new drugs. One of the conceals is a reduction in the water solubility of the compound as a result of introduction of a methyl group into two adjacent atoms foaling the ring (ortho-dimethyl group). It is usually known that the introduction of a methyl group into the compound increases the lipophilicity of the compound (Non Patent Literature 1). It is usually known that the water solubility of a compound is related with the absorption of orally administered drugs, and an increase in the lipophilicity of the compound or a reduction in the water solubility thereof may lower the absorption of drugs (Non Patent Literature 2). The other conceal is a reduction in metabolic stability. As shown in Non Patent Literatures 3 and 4, major metabolic reactions may occur in the moiety of the ortho-dimethyl group in the case of an aromatic or heteroaromatic ring substituted by an ortho-dimethyl group, and it is shown that the moiety of the ortho-dimethyl group is quickly metabolized and the half-life becomes short in humans in the case of the drug for stroke, tetramethylpyrazine (Non Patent Literature 5).

For this reason, novel bioisosteres of the heteroaromatic compounds having an ortho-dimethyl group, namely, compounds having the same pharmacological effects and having reduced concerns about the reduction in water solubility and the reduction in metabolic stability have been required, and furthermore, compounds used as synthetic intermediates for the novel bioisosteres have also been required.

Meanwhile, the compounds described in Patent Literatures 3 and 4 and Non Patent Literatures 6 to 9 are known as compounds similar to the compounds according to the invention of the present application; however, synthesizable heterocyclic rings and substituents thereof have been limited using multi-step synthetic procedures. As a result, there is a limit to synthesize heterocyclic rings having a wide variety of substituents.

CITATION LIST

Patent Literature

Patent Literature 1: International Publication No. WO 2006/124324
Patent Literature 2: WO 1996/005177
Patent Literature 3: WO 2008/128942
Patent Literature 4: JP 2010-155827A

Non Patent Literature

Non Patent Literature 1: Bioorganic & Medicinal Chemistry vol. 13, pp. 6678-6684; 2005.
Non Patent Literature 2: Pharmaceutical Science & Technology Today vol. 1, pp. 387-393; 1998.
Non Patent Literature 3: Journal of Chromatography B vol. 813, 263-268; 2004.
Non Patent Literature 4: European journal of drug metabolism and pharmacokinetics vol. 17, pp. 13-20; 1992.
Non Patent Literature 5: Zhongguo Yi Xue Ke Xue Yuan Xue Bao. vol. 18, pp. 288-91; 1996.
Non Patent Literature 6: Bioorganic & Medicinal Chemistry Letters vol. 17, 4914-4919; 2007.
Non Patent Literature 7: Tetrahedron Letters vol. 27, pp. 3045-3048; 1986.
Non Patent Literature 8: Journal of the Chemical Society B: Physical Organic pp. 289-296; 1971.
Non Patent Literature 9: Comptes Rendus des Seances de l'Academie des Sciences, Serie C: Sciences Chimiques vol. 263, pp. 429-31; 1966.

SUMMARY OF INVENTION

Technical Problem

A problem to be solved by the present invention is to provide novel bioisosteres of compounds having ortho-dimethyl heteroaromatic rings and the synthetic intermediate for the novel bioisosteres.

Solution to Problem

As a result of extensive research, the present inventors have completed the present invention. Namely, the present invention relates to [1] to [13] below.

[1] A compound represented by the formula (I) or a salt thereof:

wherein the ring Z is a 5- or 6-membered heteroaromatic ring having one or two heteroatoms in the ring;
$X^1$ is a hydrogen atom, a hydroxy group, a hydroxy $C_{1-6}$ alkyl group, $-B(OH)_2$, a boronate ester group, a cyclic boronate ester group, a boranyl group, a cyclic boranyl group, $-BF_3M_{n1}$ wherein n1 is 0 or 1 and M is an alkali metal, $-Sn(R^{12})(R^{13})(R^{14})$ wherein $R^{12}$, $R^{13}$, and $R^{14}$ are the same or different and are a $C_{1-6}$ alkyl group, -L wherein L is a leaving group, a carboxy group, a formyl group, or $-NR^{16}R^{17}$ wherein $R^{16}$ and $R^{17}$ are the same or different and are a hydrogen atom, a $C_{1-6}$ alkyl group, or a protecting group for an amino group, or is a protecting group for an amino group with the nitrogen atom bonded to $R^{16}$ and $R^{17}$; and
$X^2$ is a hydrogen atom or $-CO_2R^{18}$ wherein $R^{18}$ is a hydrogen atom, a $C_{1-6}$ alkyl group, or a protecting group for a carboxy group;
provided that a case wherein $X^1$ and $X^2$ are hydrogen atoms at the same time and the following compounds are excluded:
5,7-dihydro-furo[3,4-b]pyridin-3-amine,
5,7-dihydro-furo[3,4-b]pyridin-2(1H)-one,
3-bromo-5,7-dihydro-furo[3,4-b]pyridine,
5,7-dihydro-furo[3,4-b]pyridine-2-carboxylic acid,
5,7-dihydro-furo[3,4-b]pyridine-3-carboxylic acid,
1,3-dihydro-furo[3,4-c]pyridine-6-carboxaldehyde,
1,3-dihydro-furo[3,4-c]pyridin-6-ylmethanol, 3,4-dihydro-furo[3,4-b]pyrazin-2(1H)-one,
4-chloro-5,7-dihydro-furo[3,4-d]pyrimidine,
2-chloro-5,7-dihydro-furo[3,4-d]pyrimidine,
5,7-dihydro-furo[3,4-d]pylidazin-1(2H)-one,
2-bromo-4,6-dihydro-thieno[2,3-c]furan,
3-bromo-4,6-dihydro-thieno[2,3-c]furan,
4,6-dihydro-furo[3,4-b]furan-3-carboxylic acid,
4,6-dihydro-1H-furo[3,4-c]pyrazole-3-carboxylic acid,
3-bromo-4,6-dihydro-furo[3,4-d]isoxazole, and
4,6-dihydro-furo[3,4-d]isoxazole-3-carboxylic acid.

[2] A compound represented by the formula (II) or a salt thereof:

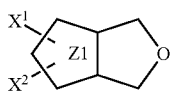

(II)

wherein the ring Z1 is a 5-membered heteroaromatic ring having one or two heteroatoms in the ring; and
$X^1$ and $X^2$ are the same as defined as in [1];
provided that a case wherein $X^1$ and X' are hydrogen atoms at the same time and the following compounds are excluded:
2-bromo-4,6-dihydro-thieno[2,3-c]furan,
3-bromo-4,6-dihydro-thieno[2,3-c]furan,
4,6-dihydro-furo[3,4-b]furan-3-carboxylic acid,
4,6-dihydro-1H-furo[3,4-c]pyrazole-3-carboxylic acid,
3-bromo-4,6-dihydro-furo[3,4-d]isoxazole, and
4,6-dihydro-furo[3,4-d]isoxazole-3-carboxylic acid.

[3] The compound or the salt thereof according to [2], wherein the ring Z1 of the compound represented by the formula (II) or the salt thereof is a thiophene ring, a furan ring, a pyrrolidine ring, a thiazole ring, an oxazole ring, an imidazole ring, an isothiazole ring, an isoxazole ring, or a pyrazole ring.

[4] The compound or the salt thereof according to [2], wherein the fused ring consisting of the ring Z1 and the adjacent ring thereto of the compound represented by the formula (II) or the salt thereof is a thieno[2,3-c]furan ring, a furo[2,3-c]furan ring, a furo[3,4-b]pyrrole ring, a furo[3,4-d]thiazole ring, a furo[3,4-d]oxazole ring, a furo[3,4-d]imidazole ring, a furo[3,4-d]isothiazole ring, a furo[3,4-d]isoxazole ring, or a furo[3,4-c]pyrazole ring in the compound represented by the formula (II) or the salt thereof.

[5] A compound represented by the formula (III) or a salt thereof:

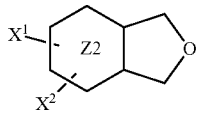

(III)

wherein the ring Z2 is a 6-membered heteroaromatic ring having one or two heteroatoms in the ring; and $X^1$ and X' are the same as defined as in [1];
provided that a case wherein $X^1$ and $X^2$ are hydrogen atoms at the same time and the following compounds are excluded:
5,7-dihydro-furo[3,4-b]pyridin-3-amine,
5,7-dihydro-furo[3,4-b]pyridin-2(1H)-one,
3-bromo-5,7-dihydro-furo[3,4-b]pyridine,
5,7-dihydro-furo[3,4-b]pyridine-2-carboxylic acid,
5,7-dihydro-furo[3,4-b]pyridine-3-carboxylic acid,
1,3-dihydro-furo[3,4-c]pyridine-6-carboxaldehyde,
1,3-dihydro-furo[3,4-c]pyridin-6-ylmethanol,
3,4-dihydro-furo[3,4-b]pyrazin-2(1H)-one,
4-chloro-5,7-dihydro-furo[3,4-d]pyrimidine,
2-chloro-5,7-dihydro-furo[3,4-d]pyrimidine, and
5,7-dihydro-furo[3,4-d]pyridazin-1(2H)-one.

[6] The compound or the salt thereof according to [5], wherein the ring Z2 is a pyridine ring, a pyrazine ring, a pyrimidine ring, or a pyridazine ring in the compound represented by the formula (III) or the salt thereof.

[7] The compound or the salt thereof according to [5], wherein a fused ring consisting of the ring Z2 and an adjacent ring thereto is a furo[3,4-b]pyridine ring, a furo[3,4-c]pyridine ring, a furo[3,4-b]pyrazine ring, a furo[3,4-d]pyrimidine ring, a furo[3,4-b]pyridazine ring, or a furo[3,4-d]pyridazine ring in the compound represented by the formula (III) or the salt thereof.

[8] The compound or the salt thereof according to any of [1] to [7], wherein $X^1$ is —B(OH)$_2$, a boronate ester group, a cyclic boronate ester group, —BF$_3$M$_{n1}$ wherein n1 is 0 or 1 and M is an alkali metal, —Sn(R$^{12}$)(R$^{13}$)(R$^{14}$) wherein R$^{12}$, R$^{13}$, and R$^{14}$ are the same or different and are a C$_{1-6}$ alkyl group, or -L wherein L is a leaving group.

[9] The compound or the salt thereof according to [8], wherein the leaving group is a halogen atom, a methanesulfonyloxy group, a p-toluenesulfonyloxy group, or a trifluoromethanesulfonyloxy group.

[10] The compound or the salt thereof according to any of [1] to [8], wherein the boronate ester group is a substituent represented by the formula (Y-1),
the cyclic boronate ester group is a substituent represented by the formulae (Y-2) to (Y-13),
the boranyl group is a substituent represented by the formula (Y-14), and
the cyclic boranyl group is a substituent represented by the formula (Y-15):

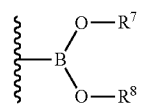

(Y-1)

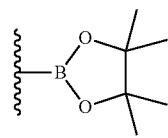

(Y-2)

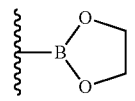

(Y-3)

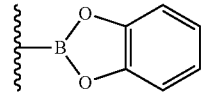

(Y-4)

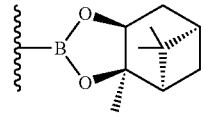

(Y-5)

-continued (Y-6) 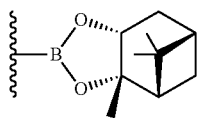

(Y-7) 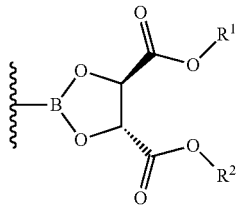

(Y-8) 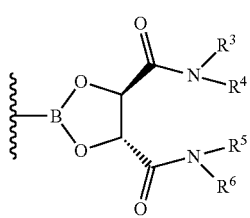

(Y-9) 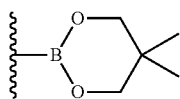

(Y-10) 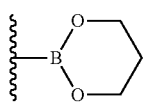

(Y-11) 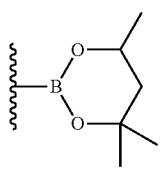

(Y-12) 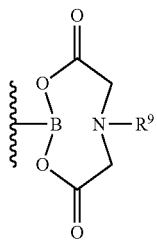

(Y-13) 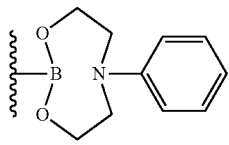

(Y-14) 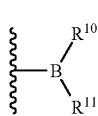

(Y-15) 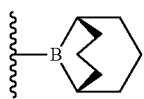

wherein $R^1$ to $R^{10}$ are the same or different and are a $C_{1-6}$ alkyl group.

[11] A compound listed below:
1,2,5,7-tetrahydro-furo[3,4-d]pyridazin-1-one,
methyl 4,6-dihydrofuro[3,4-b]furan-2-carboxylate,
4,6-dihydrofuro[3,4-b]furan-2-carboxylic acid,
4,6-dihydrothieno[2,3-c]furan-2-carbaldehyde,
(4,6-dihydrothieno[2,3-c]furan-2-yl)methanol,
2-amino-5,7-dihydrofuro[3,4-b]pyrazine,
2-amino-5,7-dihydrofuro[3,4-b]pyridine,
methyl 4,6-dihydro-1H-furo[3,4-b]pyrrole-2-carboxylate,
tert-butyl N-[(tert-butoxy)carbonyl]-N-{1,3-dihydrofuro[3,4-c]pyridin-6-yl}carbamate,
methyl 4,6-dihydrofuro[3,4-d]isothiazole-3-carboxylate,
methyl 3-amino-5,7-dihydrofuro[3,4-b]pyrazine-2-carboxylate,
methyl 3-hydroxy-4,6-dihydrothieno[2,3-c]furan-2-carboxylate,
2-chloro-4,6-dihydrothieno[2,3-c]furan,
4-amino-5,7-dihydrofuro[3,4-d]pyrimidine,
1-bromo-5,7-dihydrofuro[3,4-d]pyridazine,
lithium 3-amino-5,7-dihydrofuro[3,4-b]pyraime-2-carboxylate,
3-chloro-5,7-dihydrofuro[3,4-b]pyridine,
3-(4,4,5,5-tetramethyl-1,3,2-dioxaborolan-2-yl)-5,7-dihydrofuro[3,4-b]pyridine,
3-(tributylstannyl)-5,7-dihydrofuro[3,4-b]pyridine,
methyl 5,7-dihydrofuro[3,4-b]pyridine-3-carboxylate,
1,3-dihydrofuro[3,4-c]pyridine-6-amine,
6-bromo-1,3-dihydrofuro[3,4-c]pyridine,
5,7-dihydrofuro[3,4-d]pyrimidine-2-amine,
2-chloro-5,7-dihydrofuro[3,4-d]pyrimidine,
2-(tributylstannyl)-5,7-dihydrofuro[3,4-d]pyrimidine,
2-chloro-5,7-dihydrofuro[3,4-b]pyrazine,
2-(tributylstannyl)-5,7-dihydrofuro[3,4-b]pyrazine,
potassium (5,7-dihydrofuro[3,4-b]pyridin-3-yl)trifluoroborate,
2-chloro-5,7-dihydrofuro[3,4-b]pyridine,
2-bromo-5,7-dihydrofuro[3,4-b]pyridine,
2-(tributylstannyl)-5,7-dihydrofuro[3,4-b]pyridine,
1-chloro-5,7-dihydrofuro[3,4-d]pyridazine,
4-chloro-5,7-dihydrofuro[3,4-d]pyrimidine,
ethyl 4,6-dihydrothieno[2,3-c]furan-2-carboxylate,
methyl 1,3-dihydrofuro[3,4-c]pyridine-4-carboxylate,
1,3-dihydrofuro[3,4-c]pytidine-4-carboxylic acid,
tert-butyl (1,3-dihydrofuro[3,4-c]pyridin-4-yl)carbamate, or
1,3-dihydrofuro[3,4-c]pyridine-4-amine.

[12] A compound represented by the formula (IV):

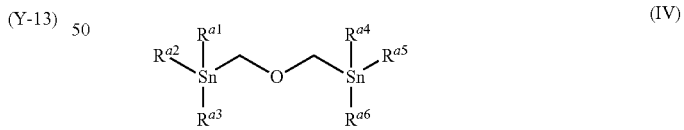

(IV)

wherein $R^{a1}$ to $R^{a6}$ are the same or different and is a $C_{1-6}$ alkyl group.

[13] A method of producing a compound represented by the formula (I):

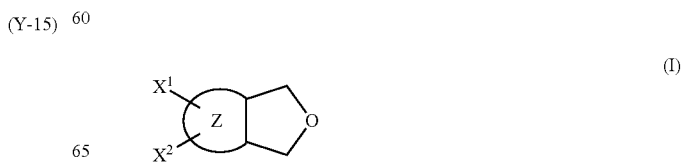

(I)

wherein the ring Z, and $X^2$ are the same as defined as in [1];
the method comprising reacting a compound represented by the formula (IV):

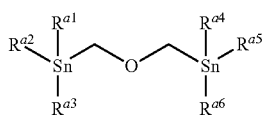
(IV)

wherein $R^{a1}$ to $R^{a6}$ are the same as defined as in [12] with a compound represented by the formula (V):

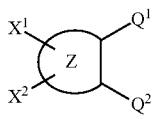
(V)

wherein the ring Z, $X^1$, and $X^2$ are the same as defined as in [1]; and $Q^1$ and $Q^2$ are a leaving group.

Advantageous Effects of Invention

The compound represented by the formula (I) (hereinafter also referred to as "compound (I)" etc.) or salts thereof can provide novel bioisosteres of compounds having ortho-dimethyl heteroaromatic rings and the synthetic intermediate products thereof. The present invention can provide methods of producing the synthetic intermediate products.

DESCRIPTION OF EMBODIMENTS

Meanings of symbols and terms used in this specification will now be described, and the present invention will be described in detail.

In this specification, although the structural formula of a compound may represent a certain isomer for convenience, the present invention includes all of isomers, such as the geometric isomers generated due to the structure of the compound, optical isomers generated based on an asymmetric carbon, stereoisomers, and tautomers, and isomer mixtures thereof; the compound is not limited by the formula expressed for convenience, and may be one of isomers or may be a mixture thereof. Accordingly, optically active compounds and racemates having an asymmetric carbon atom in the molecule may be present in the compound according to the present invention; these are not limited in the present invention and both thereof are encompassed. The polymorphism may be present in crystals, but is not limited, either; the crystals may have a single shape or the mixed crystal shapes; and the compound according to the present invention includes anhydrides, hydrates, and solvates thereof.

The compound according to the present invention includes not only free bases but also salts thereof. The "salt" in this specification is any substance which forms a salt with the compound represented by the formula (I) etc. and is not particularly limited; examples thereof include inorganic acid salts such as a hydrochloric acid salt, a hydrobromic acid salt, and a phosphoric acid salt; organic acid salts such as an acetic salt, a carbonate, and a p-toluenesulfonic acid salt; inorganic base salts such as a lithium salt, a sodium salt, and a calcium salt; organic base salts such as a pyridinium salt and a tetrabutylammonium salt; salts of acidic amino acid such as glutamic acid; and salts of basic amino acid such as arginine.

Meanings of terms and symbols used in this specification will now be described, and the present invention will be described in detail.

The "$C_{1-6}$ alkyl group" in this specification is a linear or branched alkyl group having 1 to 6 carbon atoms, and specific examples thereof include a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 1-hexyl group, a 2-hexyl group, and a 3-hexyl group.

The "hydroxy $C_{1-6}$ alkyl group" in this specification is a $C_{1-6}$ alkyl group having a hydroxy group, and examples thereof include a hydroxymethyl group.

The "halogen atom" in this specification is a fluorine atom, a chlorine atom, a bromine atom, or an iodine atom.

Examples of the "boronate ester group" in this specification include a substituent represented by the following formula (Y-1):

(Y-1)

wherein $R^7$ and $R^8$ are the same or different and is a $C_{1-6}$ alkyl group.

Examples of the "cyclic boronate ester group" in this specification include substituents represented by the following formulae (Y-2) to (Y-13):

(Y-2)

(Y-3)

(Y-4)

(Y-5)

(Y-6)

-continued (Y-7)
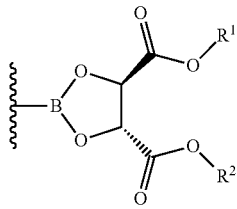

(Y-8)
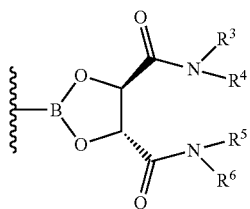

(Y-9)
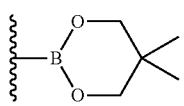

(Y-10)
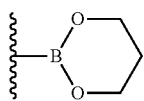

(Y-11)
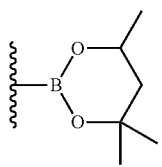

(Y-12)
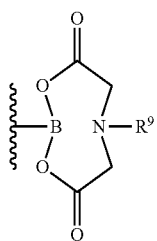

(Y-13)
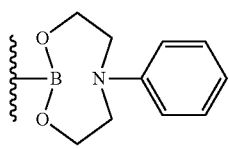

wherein $R^1$ to $R^6$ and $R^9$ are the same or different and is a $C_{1-6}$ alkyl group.

Examples of the "boranyl group" in this specification include a substituent represented by the following formula (Y-14):

(Y-14)
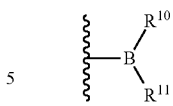

wherein $R^{10}$ and $R^{11}$ are the same or different and represent a $C_{1-6}$ alkyl group.

Examples of the "cyclic boranyl group" in this specification include a substituent represented by the following formula (Y-15):

(Y-15)

The "5- or 6-membered heteroaromatic ring having one or two heteroatoms in the ring" in this specification is an aromatic monocyclic group consisting of 5 or 6 atoms to form the ring wherein one or two of the atoms forming the ring are heteroatoms selected from an oxygen atom, a sulfur atom, and a nitrogen atom. Examples of such 5- or 6-membered heteroaromatic rings include a furyl group, a thienyl group, a pyrrolyl group, an imidazolyl group, a pyrazolyl group, an oxazolyl group, an isoxazolyl group, a thiazolyl group, an isothiazolyl group, a pyridyl group, a pyrazinyl group, a pyridazinyl group, and a pyrimidinyl group.

The "leaving group" in this specification can be any group readily eliminated from a compound represented by the formula (I) or (V) to form a new bond when the compound is fed to the subsequent reaction as a starting material, and examples thereof include a halogen atom, a methanesulfonyloxy group, a p-toluenesulfonyloxy group, and a trifluoromethanesulfonyloxy group. Preferred examples of leaving groups include a halogen atom, and more preferred is a chlorine atom Examples of the "protecting group for the carboxy group" in this specification include protecting groups for carboxylic acid usually known to those skilled in the art. Examples of protected carboxy groups include trialkylsilyl ester, tert-butyl ester, benzyl ester, and oxazoline.

The "protecting group for an amino group" in this specification include the protecting groups for an amino group usually known to those skilled in the art, and examples thereof include amide-type protecting groups such as a formyl group, an acetyl group, a benzoyl group, a nicotinoyl group, a trichloroacetyl group, or a trifluoroacetyl group; cyclic imide-type protecting groups such as a phthaloyl group or a 2,3-diphenylmaleoyl group; sulfonamide-type protecting groups such as a p-toluenesulfonyl group; or carbamate-type protecting groups such as a tert-butyloxycarbonyl group, a methyloxycarbonyl group, an ethyloxycarbonyl group, a benzyloxycarbonyl group, an allyloxycarbonyl group, a p-methoxybenzylcarbonyl group, a p-nitrobenzyloxycarbonyl group, or a 9-fluorenylmethyloxycarbonyl group; preferred is a formyl group, a tert-butyloxycarbonyl group, or a phthaloyl group.

The ring Z in the compound represented by the formula (I) etc. is a 5- or 6-membered heteroaromatic ring having one or two heteroatoms in the ring; if the ring Z1 in a compound represented by the formula (II) etc. is a 5-membered ring, the ring Z1 is preferably a thiophene ring, a furan ring, a pyrrole ring, a thiazole ring, an oxazole ring, an imidazole ring, an isothiazole ring, an isoxazole ring, or a pyrazole ring; more preferably, a fused ring consisting of the ring Z1 and an adjacent ring thereto is a thieno[2,3-c]furan ring, a furo[2,3-c]furan ring, a furo[3,4-b]pyrrole ring, a furo[3,4-d]thiazole ring, a furo[3,4-d]oxazole ring, a furo[3,4-d]imidazole ring, a furo[3,4-d]isothiazole ring, a furo[3,4-d]isoxazole ring, or a furo[3,4-c]pyrazole ring; if the ring Z2 in a compound represented by the formula (III) etc. is a 6-membered ring, preferably the ring Z2 is a pyridine ring, a pyrazine ring, a pyrimidine ring, or a pyridazine ring; more preferably, a fused ring consisting of the ring Z2 and an adjacent ring thereto is a furo[3,4-b]pyfidine ring, a furo[3,4-c]pyfidine ring, a furo[3,4-b]pyrazine ring, a furo[3,4-d]pyrimidine ring, a furo[3,4-c]pyridazine ring, or a furo[3,4-d]pyridazine ring.

$X^1$ in the compound represented by the formula (I) etc. is a hydrogen atom, a hydroxy group, a hydroxy $C_{1-6}$ alkyl group, —B(OH)$_2$, a boronate ester group, a cyclic boronate ester group, a boranyl group, a cyclic boranyl group, —BF$_3$M$_{n1}$ wherein n1 is 0 or 1 and M is an alkali metal, —Sn(R$^{12}$)(R$^{13}$)(R$^{14}$) wherein $R^{12}$, $R^{13}$, and $R^{14}$ are the same or different and is a $C_{1-6}$ alkyl group, -L wherein L is a leaving group, a carboxy group, a formyl group, or —NR$^{16}$R$^{17}$ wherein $R^{16}$ and $R^{17}$ are the same or different and is a hydrogen atom, a $C_{1-6}$ alkyl group or a protecting group for an amino group, or is a protecting group for an amino group with a nitrogen atom bonded to $R^{16}$ and $R^{17}$; preferably, $X^1$ is —B(OH)$_2$, a boronate ester group, a cyclic boronate ester group, —BF$_3$M$_{n1}$ wherein n1 is 0 or 1 and M is an alkali metal, —Sn(R$^{12}$)(R$^{13}$)(R$^{14}$) wherein $R^{12}$, $R^{13}$, and $R^{14}$ are the same or different and is a $C_{1-6}$ alkyl group, or -L wherein L is a leaving group.

$X^2$ in the compound represented by the formula (I) etc. is a hydrogen atom or —CO$_2$R$^{18}$ wherein $R^{18}$ is a hydrogen atom or a $C_{1-6}$ alkyl group, preferably a hydrogen atom or a methoxycarbonyl group, more preferably a hydrogen atom.

In the compound represented by the formula (I), the case wherein $X^1$ and $X^2$ both are hydrogen atoms is excluded.

If $X^1$ in the compound represented by the formula (I) etc. is a hydroxy group, compounds having prototropic tautomeric relations are also included in the compound represented by the formula (I). Examples of such compounds include 2-pyridone and 2-pyridazinone.

$R^{a1}$ to $R^{a6}$ in the compound represented by the formula (IV) are the same or different and are a $C_{1-6}$ alkyl group; preferably all of $R^{a1}$ to $R^{a6}$ are n-butyl groups.

The compound represented by the formula (I) can be produced by a method described below, and can also be produced by the method modified by those skilled in the art based on standard knowledge. The method of producing the compound represented by the formula (I) is not limited to these methods.

Step A

This step is a step of obtaining the compound (IV). Examples of step A include a step of obtaining a compound (IV) from a compound (1a) (Step A-1), and a step of obtaining a compound (3a) from a compound (1a) (Step A-2), and then reacting the compound (3a) with a compound (2a) to obtain a compound (IV) (Step A-3).

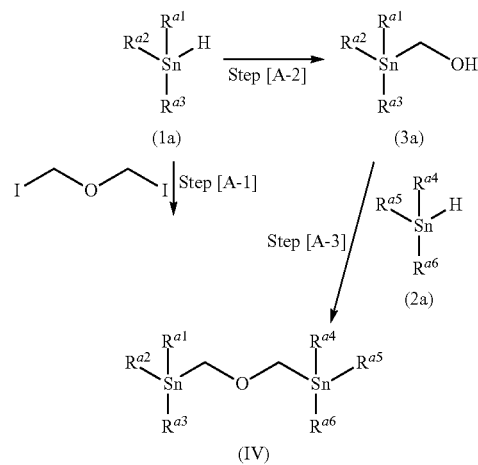

wherein $R^{a1}$ to $R^{a6}$ are the same as defined above.

[Step A-1]

Step A-1 is a step of reacting an anion generated as a result of a reaction of lithium diisopropylamide and the compound (1a) with iodo(iodomethoxy)methane to produce a compound (IV). If step A-1 is performed, step A-1 can be performed referring to the reaction conditions, operations after the reaction, purification methods, and the like described later in Production Example 1-3 and Production Example 1-4, and those skilled in the art could readily determine optimal reaction conditions and the like.

Step A-1 can also be performed under a stream or an atmosphere of an inert gas such as nitrogen or argon The solvent used in step A-1 is not particularly limited as long as the solvent can dissolve the starting material to some extent and does not inhibit the reaction to be performed in step A-1. Any solvent selected from the group consisting of ether solvents such as tetrahydrofuran, 1,2-dimethoxyethane, methyl tert-butyl ether, cyclopentyl methyl ether, diethyl ether, diisopropyl ether, dibutyl ether, and dicyclopentyl ether; aromatic hydrocarbon solvents such as benzene and toluene; aliphatic hydrocarbon solvents such as heptane and hexane; and mixed solvents thereof can be used as the solvent used in step A-1. A particularly preferred solvent is tetrahydrofuran.

The reaction time for step A-1 usually varies in consideration of the type of the starting material used, the type of the solvent, and the reaction temperature, and those skilled in the art could readily select a preferred reaction time. For example, a mixture of an anion prepared by reacting the compound (1a) with lithium diisopropylamide at 0° C. (outer temperature of the reaction container) and iodo(iodomethoxy)methane is stirred at room temperature for 1 hour.

Although a preferred reaction temperature for the reaction of the compound prepared by anionizing the compound (1a) with iodo(iodomethoxy)methane varies according to the type of the starting material used and the like as described above, it is preferred that this reaction be performed at 0° C. to room temperature (outer temperature of the reaction container), more suitably at room temperature while the mixture is being stirred.

It is preferred that 2 to 3 moles of compound (1a) be used relative to 1 mole of iodo(iodomethoxy)methane, and it is more preferred that 2 to 2.5 moles of compound (1a) be used.

It is preferred that 2 to 3 moles of lithium diisopropylamide be used relative to 1 mole of iodo(iodomethoxy)methane, and it is more preferred that 2 to 2.5 moles of lithium diisopropylamide be used.

[Step A-2]

Step A—2 is a step of reacting an anion generated as a result of a reaction of lithium diisopropylamide and the compound (1a) with paraformaldehyde to produce a compound (3a). If step A-2 is performed, step A-2 can be performed referring to the reaction conditions, operations after the reaction, and purification methods described later in Production Example 1-1, and those skilled in the art could readily determine optimal reaction conditions and the like.

Step A-2 can also be performed under a stream or an atmosphere of an inert gas such as nitrogen or argon.

The solvent used in step A-2 is not particularly limited as long as the solvent can dissolve the starting material to some extent and does not inhibit the reaction to be performed in step A-2. Any solvent selected from the group consisting of ether solvents such as tetrahydrofuran, 1,2-dimethoxyethane, methyl tert-butyl ether, cyclopentyl methyl ether, diethyl ether, diisopropyl ether, dibutyl ether, and dicyclopentyl ether; aromatic hydrocarbon solvents such as benzene and toluene; aliphatic hydrocarbon solvents such as heptane and hexane; and mixed solvents thereof can be used as the solvent used in step A-2. A particularly preferred solvent is tetrahydrofuran.

The reaction time for step A-2 usually varies in consideration of the type of the starting material used, the type of the solvent, and the reaction temperature, and those skilled in the art could readily select a preferred reaction time. For example, a mixture of an anion prepared from the compound (1a) and lithium diisopropylamide at 0° C. (outer temperature of the reaction container) with paraformaldehyde is stirred at room temperature for 30 minutes.

Although a preferred reaction temperature for the reaction of the compound prepared by anionizing the compound (1a) with paraformaldehyde varies according to the type of the starting material used and the like as described above, it is preferred that this reaction be performed at 0° C. to room temperature (outer temperature of the reaction container), more suitably at room temperature while the mixture is being stirred.

It is preferred that 1 to 1.5 moles of lithium diisopropylamide be used relative to 1 mole of compound (1a), and it is more preferred that 1 to 1.1 moles of lithium diisopropylamide be used.

It is preferred that 1 to 1.5 moles of paraformaldehyde be used relative to 1 mole of compound (1a), and it is more preferred that 1 to 1.2 moles of paraformaldehyde be used.

[Step A-3]

Step A-3 is a step of preparing tributyl((chloromethoxy)methyl)stannane from the compound (3a), paraformaldehyde and chlorotrimethylsilane, and adding an anion generated as a result of the reaction of lithium diisopropylamide and the compound (2a) to the compound to produce a compound (IV). If step A-3 is performed, step A-3 can be performed referring to the reaction conditions, operations after the reaction, and purification methods described later in Production Example 1-2, and those skilled in the art could readily determine optimal reaction conditions and the like.

Step A-3 can also be performed under a stream or an atmosphere of an inert gas such as nitrogen or argon The solvent used in step A-3 is not particularly limited as long as the solvent can dissolve the starting material to some extent and does not inhibit the reaction to be performed in step A-3. Any solvent selected from the group consisting of ether solvents such as tetrahydrofuran, 1,2-dimethoxyethane, methyl t-butyl ether, cyclopentyl methyl ether, diethyl ether, diisopropyl ether, dibutyl ether, and dicyclopentyl ether; aromatic hydrocarbon solvents such as benzene and toluene; aliphatic hydrocarbon solvents such as heptane and hexane; and mixed solvents thereof can be used as the solvent used in step A-3. A particularly preferred solvent is tetrahydrofuran.

The reaction time for step A-3 usually varies in consideration of the type of the starting material used, the type of the solvent, and the reaction temperature, and those skilled in the art could readily select a preferred reaction time. For example, the reaction time to prepare tributyl((chloromethoxy)methyl)stannane from the compound (3a), paraformaldehyde, and chlorotrimethylsilane is 2 to 3 hours at room temperature. The time for the reaction of the anionized compound prepared from the compound (1a) and lithium diisopropylamide at 0° C. (outer temperature of the reaction container) with tributyl((chloromethoxy)methyl)stannane is 1 hour at room temperature.

Although the reaction temperature to prepare tributyl ((chloromethoxy)methyl)stannane from the compound (3a), paraformaldehyde, and chlorotrimethylsilane varies in consideration of the type of the starting material used and the like as described above, the reaction temperature is suitably room temperature. Although a preferred reaction temperature for the reaction of the compound prepared by anionizing the compound (1a) with tributyl((chloromethoxy)methyl) stannane varies in consideration of the type of the starting material used and the like as described above, the reaction temperature is suitably room temperature.

It is preferred that 1 mole of compound (3a), a solvent amount of chlorotrimethylsilane, 2 moles of compound (1a), and 2 moles of lithium diisopropylamide be used relative to 1 mole of paraformaldehyde.

Step B

This step is a step of obtaining a compound (I).

[Step B-1]

Step B-1 is a step of producing a compound (I) through a coupling reaction between a compound (V) and a compound (IV) in an appropriate solvent.

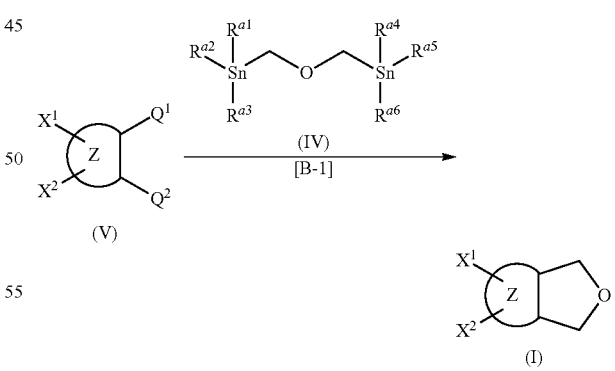

wherein the ring Z, $X^1$, $X^2$, $R^{a1}$ to $R^{a6}$, $Q^1$ and $Q^2$ are the same as defined above.

The reaction can also be performed under a stream or an atmosphere of an inert gas such as nitrogen or argon Any compound selected from commercially available compounds, and known compounds, or compounds which can be produced from these compounds by any known method can be used as the compound (V).

Step B-1 is performed in the presence of a metal catalyst which is effective as a catalyst for the reaction. It is preferred that the metal catalyst be particularly a palladium catalyst. Specific examples of the palladium catalyst include palladium(II) acetate, tris(dibenzylideneacetone)dipalladium(0), bis(dibenzylideneacetone)palladium(0), palladium on carbon, bis(triphenylphosphine)palladium(II) chloride, and tetrakis(triphenylphosphine)palladium(0); palladium(II) acetate, tris(dibenzylideneacetone)dipalladium(0), and bis(dibenzylideneacetone)palladium(0) are particularly preferred.

It is preferred that the metal catalyst be used in an amount of 0.001 to 0.5 mol relative to 1 mole of compound (V), and it is more preferred that the metal catalyst be used in an amount of 0.05 to 0.2 mol.

It is particularly preferred that step B-1 be performed in the presence of a phosphine compound with the metal catalyst. To obtain good results, a halogen compound such as lithium chloride or a silicon compound such as tert-butyldimethylchlorosilane can also be added.

Examples of the phosphine compound include triphenylphosphine,
2-dicyclohexylphosphino-2',6'-dimethoxybiphenyl,
2-dicyclohexylphosphino-2',6'-diisopropoxybiphenyl,
2-dicyclohexylphosphino-2',4',6'-triisopropylbiphenyl, and
2-[bis[3,5-bis(trifluoromethyl)phenyl]phosphino]-3,6-dimethoxy-2',4',6'-triisopropyl-1,1'-biphenyl; 2-dicyclohexylphosphino-2',4',6'-triisopropylbiphenyl is particularly preferred.

It is preferred that the amount of the phosphine compound to be used be 0.001 to 2 mol relative to 1 mole of compound (V), and it is more preferred that the amount of the phosphine compound to be used be 0.05 to 0.8 mol.

As the halogen compound, lithium chloride, tetrabutylammonium chloride, and potassium iodide are particularly preferred. It is preferred that the amount of the halogen compound to be used be 1 to 3 mol relative to 1 mole of compound (V).

As the silicon compound, tert-butyldimethylchlorosilane is particularly preferred. It is preferred that the amount of the silicon compound be 1 to 2 mol relative to 1 mole of compound (V).

In step B-1, it is preferred that the compound (IV) be used in an amount of 1 to 1.5 mol relative to 1 mole of compound (V), and it is more preferred that the compound (IV) be used in an amount of 1 to 1.2 mol equivalents.

The solvent used in step B-1 is not particularly limited as long as the solvent can dissolve the starting raw material to some extent and does not inhibit the reaction.

Examples of the solvent include ether solvents such as tetrahydrofuran, 1,2-dimethoxyethane, methyl tert-butyl ether, cyclopentyl methyl ether, diethyl ether, diisopropyl ether, dibutyl ether, and dicyclopentyl ether; aromatic hydrocarbon solvents such as benzene and toluene; aliphatic hydrocarbon solvents such as heptane and hexane; amide solvents such as N,N-dimethylformamide and N-methylpyrrolidinone; and mixed solvents thereof; a particularly preferred solvent is 1,4-dioxane.

For specific reaction conditions, treatments after the reaction, and purification methods in step B-1, those skilled in the art could readily determine the optimal conditions to the reaction referring to the conditions described later in Example 1, Example 2, Example 4, and Examples 6 to 14 even if another starting material other than those shown in Examples is used.

Although the reaction temperature and the reaction time in step B-1 vary in consideration of the type of the starting material used, the type of the solvent used, and the reaction temperature, those skilled in the art can readily determine the optimal reaction temperature and reaction time. It is preferred that the reaction temperature be usually 50° C. to 150° C. (outer temperature of the reaction container), and it is more preferred that the reaction temperature be 80° C. to 140° C. (outer temperature of the reaction container). Usually, it is preferred that after all of starting materials are mixed, the reaction be performed for 1 to 72 hours under stirring, and it is more preferred that after all of starting materials are mixed, the reaction be performed for 1 to 20 hours under stirring.

[Step B-2 to Step B-8]

Compounds (I-1) to (I-5) wherein $X^1$ in the compound (1) is a hydroxy group, —$B(OH)_2$, a boronate ester group, a cyclic boronate ester group, a boranyl group, a cyclic boranyl group, —$BF_3M_{n1}$, —$Sn(R^{12})(R^{13})(R^{14})$, or a leaving group can also be produced through step B-2 to step B-8 below:

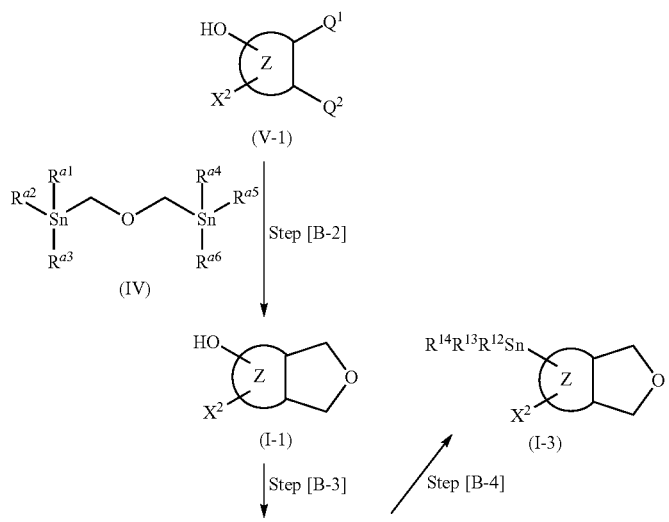

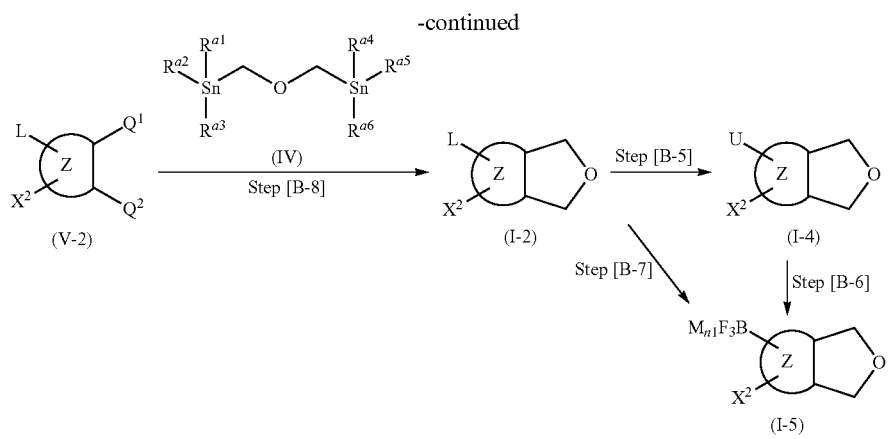

wherein the ring Z, $X^2$, $R^{a1}$ to $R^{a6}$, $R^{12}$ to $R^{14}$, L, and n1 are the same as defined above; and U is —$B(OH)_2$, a boronate ester group, a cyclic boronate ester group, a substituted boranyl group, or a cyclic boranyl group.

[Step B-2]

Step B-2 is a step of producing a compound (I-1) through a coupling reaction between a compound (V-1), in which $X^1$ in the compound (V) is a hydroxy group, and a compound (IV). Any compound selected from commercially available compounds, and known compounds, or compounds which can be produced from these compounds by any known method can be used as the compound (V-1). This step can be performed on the same conditions as those in step B-1.

Before and after this step, the hydroxy group of the compound (V-1) may be protected with an appropriate protecting group or may be deprotected if necessary.

The step of protecting a hydroxy group and the step of deprotecting the protecting group for the hydroxy group can be performed by a method usually used by those skilled in the art, such as a method described in Protective Groups in Organic Synthesis, third edition, pp. 246-287, 1999, JOHN WILEY & SONS, INC. For the type of the protecting group, an ether protecting group such as tert-butyldimethylsilyl ether or methoxymethyl ether or an ester protecting group such as pivalate can be used.

[Step B-3]

Step B-3 is a step of converting a hydroxy group of a compound (I-1) into a leaving group such as a trifluoromethanesulfonyloxy group to produce a compound (I-2). This step can be performed by a method usually used by those skilled in the art such as methods described in Synthesis, Vol. 44, pp. 1631-1636; 2012, Tetrahedron Letters, Vol. 53, pp. 377-379; 2012, Tetrahedron Letters, Vol. 52, pp. 6346-6348; 2011, Journal of Medicinal Chemistry, Vol. 55, pp. 10610-10629; 2012, Journal of Medicinal Chemistry, Vol. 55, pp. 10475-10489; 2012, Journal of Medicinal Chemistry, Vol. 54, pp. 8174-8187; 2011, and Journal of Heterocyclic Chemistry, Vol. 22, pp. 1621-1630; 1985. More specifically, this step can be performed referring to the reaction conditions, operations after the reaction, and purification methods described later in Example 14.

[Step B-4]

Step B-4 is a step of converting a leaving group of a compound (I-2) into a substituted stannyl group to produce a compound (I-3). This step can be performed by a method usually used by those skilled in the art such as methods described in Synthesis, Vol. 44, pp. 3496-3504; 2012, Organic Letters, Vol. 14, pp. 4630-4633; 2012, Synthesis, Vol. 44, pp. 2959-2963; 2012, Tetrahedron, Vol. 69, pp. 902-909; 2013, Journal of the American Chemical Society, Vol. 133, pp. 17777-17785; 2011, and Chemistry—A European Journal, Vol. 18, pp. 5565-5573; 2012.

[Step B-5]

Step B-5 is a step of converting a leaving group of a compound (I-2) into a boron-containing substituent such as a boronate ester group to produce a compound (I-4). This step can be performed by a method usually used by those skilled in the art such as methods described in Chemical & Pharmaceutical Bulletin, Vol. 31, pp. 4573; 1982, Journal of Medicinal Chemistry, Vol. 51, pp. 6280-6292; 2008, Journal of Organometallic Chemistry, Vol. 292, pp. 119-132; 1985, Tetrahedron Letters, Vol. 53, pp. 4873-4876; 2012, Journal of Medicinal Chemistry, Vol. 51, pp. 6280-6292; 2008, and European Journal of Organic Chemistry, No. 7, pp. 1678-1684; 2006.

[Step B-6]

Step B-6 is a step of converting a boron-containing substituent of a compound (I-4) into a trifluoroboron substituent to produce a compound (I-5). This step can be performed by a method usually used by those skilled in the art such as methods described in Journal of Medicinal Chemistry, Vol. 54, pp. 6761-6770; 2011, Organic Letters, Vol. 14, pp. 5058-5061; 2012, and Tetrahedron, Vol. 69, pp. 1546-1552; 2013.

[Step B-7]

Step B-7 is a step of converting a leaving group of a compound (I-2) into a trifluoroboron substituent to produce a compound (1-5). This step can be performed by a method usually used by those skilled in the art such as methods described in Organic Letters, Vol. 14, pp. 4814-4817; 2012, Journal of the American Chemical Society, Vol. 134, pp. 11667-11673; 2012, Journal of the American Chemical Society, Vol. 132, pp. 17701-17703; 2010, Tetrahedron, Vol. 68, pp. 1351-1358; 2012, Organic Letters, Vol. 14, pp. 5058-5061; 2012, and Journal of Medicinal Chemistry, Vol. 54, pp. 5174-5184; 2011.

[Step B-8]

Step B-8 is step of reacting a compound (V-2), in which $X^1$ of the compound (V) is a leaving group, with a compound (IV) to produce a compound (1-2). Any compound selected from commercially available compounds, and known compounds, or compounds which can be produced from these compounds by any known method can be used as the compound (V-2). This step can be performed on the same conditions as those in step B-1.

[Step B-9 to Step B-11]

The compound (1-6) in which $X^1$ of the compound (I) is a carboxy group can also be produced through step B-9 to step B-11 below:

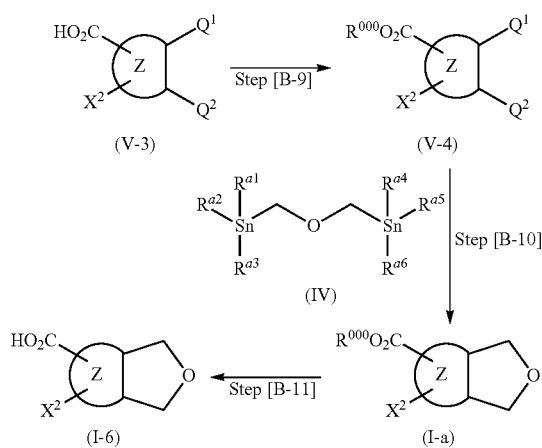

wherein the ring Z, $X^2$, $Q^1$, $Q^2$, and $R^{a1}$ to $R^{a6}$ are the same as defined above; and $R^{000}$ is a protecting group for carboxylic acid.

[Step B-9]

Step B-9 is a step of producing a compound (V-4) through protection of carboxylic acid of a compound (V-3). Commercially available compounds, known compounds and the compound (V-3) can be produced from these compounds by any known method, can be used as the compound (V-3). This step can be performed by a method usually used, such as a method described in Protective Groups in Organic Synthesis, third edition, pp. 369-451, 1999, JOHN WILEY & SONS, INC. For the type of the protecting group, an ester protecting group such as a methyl ester can be used, and any protecting group suitable for step B-10 and step B-11 can be used. More specifically, this step can be performed referring to the reaction conditions, operations after the reaction, and purification methods described later in Example 2 or Example 10.

[Step B-10]

Step B-10 is a step of producing a compound (I-a) through a coupling reaction of a compound (V-4) and a compound (IV). This step can be performed on the same conditions as those in step B-1. More specifically, this step can be performed referring to the reaction conditions, operations after the reaction, and purification methods described later in Example 2, Example 8, Example 10, Example 11, and Example 12.

[Step B-11]

Step B-11 is a step of deprotecting the protecting group for carboxylic acid of a compound (I-a) to produce a compound (1-6). This step can be performed by a method usually used by those skilled in the art, such as a method described in Protective Groups in Organic Synthesis, third edition, pp. 246-287, 1999, JOHN WILEY & SONS, INC. More specifically, this step can be performed referring to the reaction conditions, operations after the reaction, and purification methods described later in Example 3.

[Step B-12]

A compound (I-7) in which $X^1$ of the compound (I) is $NR^{16}N^{17}$ can be produced through step B-12 below:

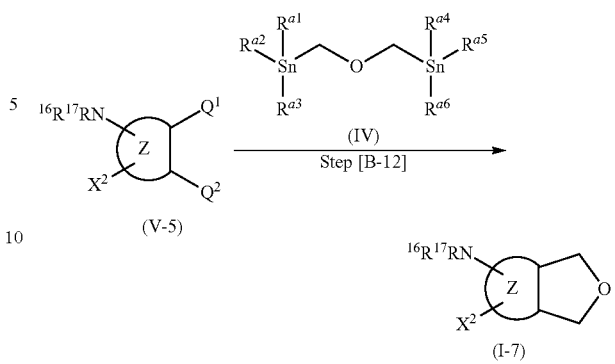

wherein the ring Z, $X^2$, $Q^1$, $Q^2$, $R^{a1}$ to $R^{a6}$, $R^{16}$, and $R^{17}$ are the same as defined above.

Commercially available compounds and known compounds can be used as the compound (V-5), or the compound (V-5) can be produced from these compounds by any known method. If at least one of $R^{16}$ and $R^{17}$ is a protecting group for an amino group, the compound (I-7) can be synthesized from the corresponding primary or secondary amine by a known method such as a method described in Protective Groups in Organic Synthesis, third edition, pp. 494-592, 1999, JOHN WILEY & SONS, INC. For the type of the protecting group, any protecting group suitable for step B-12 and its subsequent deprotection step can be used; for example, a carbamate-type protecting group such as a tert-butoxycarbonyl group or a cyclic imide-type protecting group such as N-phthalimide can be used. More specifically, protection and deprotection of amine can be performed referring to the reaction conditions, operations after the reaction, and purification methods described later in Example 9.

[Step B-12]

Step B-12 is a step of producing a compound (I-7) through a coupling reaction of a compound (V-5) and a compound (IV). This step can be performed on the same conditions as those in step B-1. More specifically, this step can be performed referring to the reaction conditions, operations after the reaction, and purification methods described later in Example 6, Example 7, Example 9, Example 11, and Example 14.

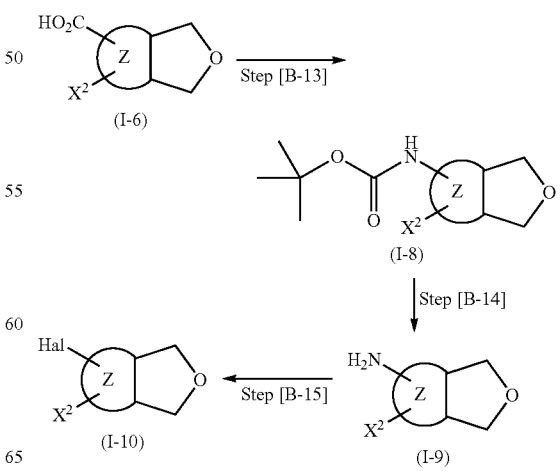

wherein the ring Z and X² are the same as defined above; and Hal is a halogen atom.

[Step B-13]

Step B-13 is a step of converting a carboxy group of a compound (I-6) into amine protected with a tert-butoxycarbonyl group to produce a compound (I-8). Commercially available compounds, known compounds, and the compound (I-6) can be produced from these compounds by any known method can be used as the compound (1-6). This step can be performed by a method usually used, such as a method described in Journal of Medicinal Chemistry, Vol. 48, pp. 1886-1900; 2005. More specifically, this step can be performed referring to the reaction conditions, operations after the reaction, and purification methods described later in Example 40.

[Step B-14]

Step B-14 is a step of deprotecting a protecting group for amine of a compound (1-8) to produce a compound (I-9). Commercially available compounds and known compounds can be used as the compound (1-8), or the compound (I-8) can be produced from these compounds by any known method. This step can be performed by a method usually used such as a method described in Protective Groups in Organic Synthesis, third edition, pp. 520-525, 1999, JOHN WILEY & SONS, INC. More specifically, this step can be performed referring to the reaction conditions, operations after the reaction, and purification methods described later in Example 41.

[Step B-15]

Step B-15 is a step of converting an amino group of a compound (1-9) into halogen to produce a compound (I-10). Commercially available compounds and known compounds can be used as the compound (1-9), or the compound (I-9) can be produced from these compounds by any known method. This step can be performed by a method usually used, such as a method described in Bioorganic and Medicinal Chemistry, Vol. 7, pp. 1845-1855; 1999. More specifically, this step can be performed referring to the reaction conditions, operations after the reaction, and purification methods described later in Example 32 and Example 33.

EXAMPLE

The present invention will be described below in more detail with reference to Examples, but the present invention is not limited to these Examples.

Chemical shifts of proton nuclear magnetic resonance spectra ($^1$H-NMR) are recorded in δ units (ppm) relative to tetramethylsilane, and coupling constants are recorded in hertz (Hz). Abbreviations for splitting patterns are as follows.

s: singlet, d: doublet, t: triplet, q: quartet, m: multiplet, br s: broad singlet.

Abbreviations used in the Examples should be understood as follows.

X-Phos: 2-dicyclohexylphosphino-2',4',6'-triisopropylbiphenyl
LCMS: Liquid chromatography mass spectrometry
DMSO: Dimethylsulfoxide
MS: Mass spectrum Example 1

1,2,5,7-Tetrahydro-furo[3,4-d]pyridazin-1-one

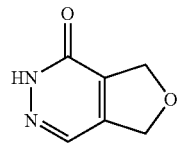

To a solution of 4,5-dichloro-2,3-dihydro-pyridazin-3-one (160 mg, 1.00 mmol) and tributyl{[(ributylstannyl)methoxyl]]methyl}stannane according to Production Example 1-2 (620 mg, 1.0 mmol) in 1,4-dioxane (10 mL), tert-butyldimethylchlorosilane (180 mg, 1.2 mmol) was added at room temperature, and the resulting mixture was stirred at the same temperature for 30 minutes. X-Phos (190 mg, 0.40 mmol) and tris(dibenzylideneacetone)dipalladium (92 mg, 0.10 mmol) were added to the reaction mixture at room temperature, and then the resulting mixture was stirred at 100° C. for 14 hours. The reaction mixture was concentrated under reduced pressure, and then the residue was purified by silica gel column chromatography (ethyl acetate:hexane=2:1) to obtain the title compound (110 mg, 78% yield).

$^1$H-NMR Spectrum (400 MHz, CDCl₃) δ (ppm): 5.09-5.14 (m, 4H), 7.86 (s, 1H), 11.45 (br s, 1H).

Tributyl {[(tributylstannyl)methoxy]methyl}stannane, the starting material, was produced by the following two synthesis methods.

Production Example 1-1

(Tributylstannyl)methanol

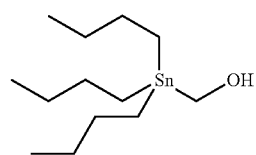

To a mixture of diisopropylamine (5.3 mL, 38 mmol) and tetrahydrofuran (120 mL), n-butyllithium (a 1.6 M solution in hexane, 22 mL, 36 mmol) was added dropwise at −78° C., and the resulting mixture was stirred at the same temperature for 30 minutes. Tributyltin hydride (9.2 mL, 34 mmol) was added dropwise to the reaction mixture at the same temperature. The reaction mixture was stirred at 0° C. for 30 minutes. The reaction mixture was cooled to −78° C., paraformaldehyde (1.2 g, 41 mmol) was added thereto, and the temperature was gradually raised to room temperature. The resulting mixture was further stirred at room temperature for 30 minutes, then water was added to the reaction mixture, and the resulting mixture was extracted with diethyl ether. The organic layer was washed with a saturated saline solution and dried over anhydrous magnesium sulfate. The solution was filtered and concentrated under reduced pressure. The residue was purified by silica gel column chromatography (ethyl acetate:heptane=1:10) to obtain the title compound (4.7 g, 43% yield).

$^1$H-NMR Spectrum (400 MHz, CDCl$_3$) δ (ppm): 0.87-0.95 (m, 15H), 1.24-1.37 (m, 6H), 1.47-1.58 (m, 6H), 3.99-4.05 (m, 2H).

Production Example 1-2

Tributyl {[(tributylstannyl)methoxy]methyl}stannane

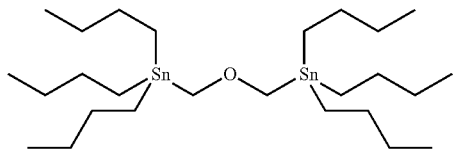 [SMILES: CCC[CH2][Sn]([CH2]CCC)([CH2]CCC)[CH2]O[CH2][Sn]([CH2]CCC)([CH2]CCC)[CH2]CCC]

A mixture of paraformaldehyde (0.10 mg, 3.1 mmol) and chlorotrimethylsilane (5.0 mL, 3.1 mmol) was stirred at room temperature for 1 hour. (Tributylstannyl)methanol according to Production Example 1-1 (1.0 g, 3.1 mmol) was added to the reaction mixture at room temperature, and the resulting mixture was stirred at the same temperature for 2 hours. The solvent was concentrated under reduced pressure to obtain crude tributyl((chloromethoxy)methyl)stannane. To a mixture of diisopropylamine (0.87 mL, 6.2 mmol) and tetrahydrofuran (10 mL), n-butyllithium (a 1.6 M solution in hexane, 3.8 mL, 6.2 mmol) was added dropwise at −78° C., and the resulting mixture was stirred at the same temperature for 30 minutes. Tributyltin hydride (1.7 mL, 6.2 mmol) was added dropwise to the reaction mixture at the same temperature, and then the resulting mixture was stirred at 0° C. for 30 minutes. The reaction mixture was cooled to −78° C., and a mixture of the crude tributyl((chloromethoxy)methyl)stannane and tetrahydrofuran (5 mL) was added dropwise at the same temperature. The reaction mixture was gradually warmed up to room temperature and further stirred at the same temperature for 1 hour. Water was added to the reaction mixture, and the resulting mixture was extracted with diethyl ether. The organic layer was washed with a saturated saline solution and dried over anhydrous magnesium sulfate. The organic layer was concentrated under reduced pressure, and the residue was purified by neutral silica gel column chromatography (ethyl acetate:heptane=1:10) to obtain the title compound (450 mg, 23% yield).

$^1$H-NMR Spectrum (400 MHz, CDCl$_3$) δ (ppm): 0.85-0.92 (m, 30H), 1.30 (dq, J=14.9, 7.2 Hz, 12H), 1.45-1.54 (m, 12H), 3.63-3.69 (m, 4H).

Another method of synthesis of tributyl {[(tributylstannyl)methoxy]methyl}stannane Production Example 1-3

Iodo(iodomethoxy)methane

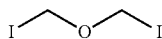

A reaction mixture of iodotrimethylsilane (25 g, 0.13 mol) and 1,3,5-trioxane (4.0 g, 44 mmol) was stirred at 40° C. for 15 hours. The reaction mixture was cooled to room temperature, and then the solvent was concentrated under reduced pressure. The residue was distilled under reduced pressure (7 mmHg, about 80° C.) to obtain the title compound (13 g, 98% yield).

$^1$H-NMR Spectrum (400 MHz, CDCl$_3$) δ (ppm): 5.71 (s, 4H).

Production Example 1-4

Tributyl{[(tributylstannyl)methoxy]methyl}stannane

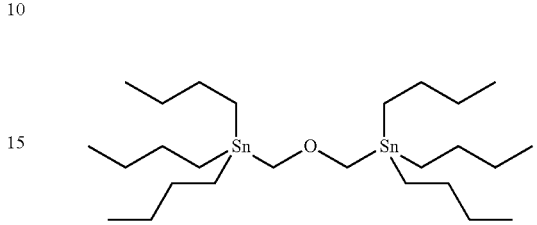

To a mixture of diisopropylamine (0.57 mL, 4.0 mmol) and tetrahydrofuran (10 mL), n-butyllithium (a 1.6 M solution in hexane, 2.5 mL, 4.0 mmol) was added dropwise at −78° C., and the resulting mixture was stirred at the same temperature for 30 minutes. Tributyltin hydride (1.1 mL, 4.0 mmol) was added dropwise to the reaction mixture at the same temperature. The reaction mixture was stirred at 0° C. for 30 minutes. The reaction mixture was cooled to −78° C., and iodo(iodomethoxy)methane according to Production Example 1-3 (500 mg, 1.7 mmol) was added at the same temperature. The reaction mixture was gradually warmed up to room temperature and stirred at the same temperature for 1 hour. Water was added to the reaction mixture, and the resulting mixture was extracted with diethyl ether. The organic layer was washed with a saturated saline solution and then dried over anhydrous magnesium sulfate. The solvent was concentrated under reduced pressure, and the residue was purified by neutral silica gel column chromatography (ethyl acetate:heptane=1:10) to obtain the title compound (0.18 g, 17% yield).

$^1$H-NMR Spectrum (400 MHz, CDCl$_3$) δ (ppm): 0.85-0.92 (m, 30H), 1.30 (dq, J=14.9, 7.2 Hz, 12H), 1.45-1.54 (m, 12H), 3.63-3.69 (m, 4H).

Example 2

Methyl 4,6-dihydrofuro[3,4-b]furan-2-carboxylate

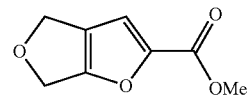 [SMILES: COC(=O)c1cc2c(o1)COC2]

To a mixture of methyl 4,5-dibromofuran-2-carboxylate according to Production Example 2-1 (50 mg, 0.18 mmol), tributyl{[tributylstannyl)methoxy]methyl}stannane according to Production Example 1-2 (110 µL, 0.18 mmol), and 1,4-dioxane (2.0 mL), bis(dibenzylideneacetone)palladium (10 mg, 18 µmol) and X-Phos (17 mg, 35 µmol) were added under a nitrogen atmosphere at room temperature. The reaction mixture was stirred at 100° C. for 10 hours. The reaction mixture was cooled to room temperature and filtered through Celite. Water was added to the filtrate, and the resulting mixture was extracted with ethyl acetate twice. The organic layers were combined, washed sequentially with water and a saturated saline solution, and dried over anhydrous sodium sulfate. The solvent was distilled off under reduced pressure, and the residue was purified by preparative thin-layer chromatography (the solvent was developed 3 times with a mixed solvent of ethyl acetate:heptane=1:8) to obtain the title compound (13 mg, 43% yield).

$^1$H-NMR Spectrum (400 MHz, CDCl$_3$) δ (ppm): 3.90 (s, 3H), 4.83-4.87 (m, 4H), 7.09 (s, 1H).

MS (ESI) m/z 168.9 (MH)$^+$.

Production Example 2-1

Methyl 4,5-dibromofuran-2-carboxylate

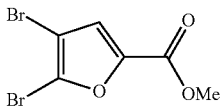

To a mixture of 4,5-dibromofuran-2-carboxylic acid (500 mg, 1.9 mmol), dichloromethane (5.0 mL), and N,N-dimethylformamide (catalytic amount), oxalyl chloride (210 μL, 2.4 mmol) was added dropwise at 0° C. The reaction mixture was stirred at room temperature for 1 hour. The solvent was distilled off under reduced pressure, and then triethylamine (340 μL, 2.4 mmol) and methanol (4.0 mL) were added, and the resulting mixture was stirred at room temperature for 1 hour. The solvent was distilled off under reduced pressure, then a saturated aqueous solution of sodium hydrogencarbonate was added, and then the resulting mixture was extracted with ethyl acetate. The organic layer was washed sequentially with water and a saturated saline solution and dried over sodium sulfate. The solvent was distilled off under reduced pressure to obtain the title compound (460 mg, 88% yield).

$^1$H-NMR Spectrum (400 MHz, CDCl$_3$) δ (ppm): 3.90 (s, 3H), 7.18 (s, 1H).

Example 3

4,6-Dihydrofuro[3,4-b]furan-2-carboxylic acid

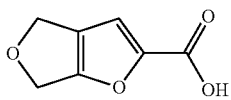 [SMILES: O=C(O)c1cc2c(o1)COC2]

To a mixture of methyl 4,6-dihydrofuro[3,4-b]furan-2-carboxylate according to Example 2 (13 mg, 75 μmol) and ethanol (2.0 mL), a 5 M aqueous solution of sodium hydroxide (30 μL) was added at room temperature, and the resulting mixture was stirred at 70° C. for 1 hour. The reaction mixture was cooled to room temperature, the solvent was distilled off under reduced pressure, and then water was added. The water layer was washed with ether, then 2 M hydrochloric acid (200 μL) was added for neutralization, and the resulting water layer was extracted with ethyl acetate twice. The organic layers were combined and dried over sodium sulfate. The solvent was distilled off under reduced pressure to obtain the title compound (8.5 mg, 74% yield).

$^1$H-NMR Spectrum (400 MHz, CDCl$_3$) δ (ppm): 4.86-4.90 (m, 4H), 7.20 (s, 1H).

Example 4

4,6-Dihydrothieno[2,3-c]furan-2-carbaldehyde

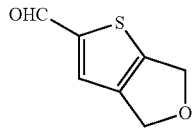

To a mixture of 4,5-dibromothiophene-2-carbaldehyde (270 mg, 1.0 mmol), tributl{[(tributylstannyl)methoxy]methyl}stannane according to Production Example 1-2 (620 mg, 1.0 mmol), N-methylpyrrolidone (10 mL), and xylene (1 mL), X-Phos (95 mg, 0.20 mmol) and tris(dibenzylideneacetone)dipalladium (92 mg, 0.10 mmol) were added at room temperature, and the resulting mixture was stirred at 80° C. for 14 hours. The reaction mixture was concentrated under reduced pressure, and then purified by silica gel column chromatography (ethyl acetate:hexane=1:5) to obtain the title compound (80 mg, 52% yield).

$^1$H-NMR Spectrum (400 MHz, CDCl$_3$) δ (ppm): 4.99 (t, J=4.0 Hz, 2H), 5.12 (t, J=4.0 Hz, 2H), 7.49 (s, 1H), 9.83 (s, 1H).

Example 5

(4,6-Dihydrothieno[2,3-c]furan-2-yl)methanol

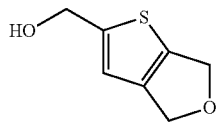

To a solution of 4,6-dihydrothieno[2,3-c]furan-2-carbaldehyde according to Example 4 (5.0 mg, 0.032 mmol) in tetrahydrofuran (0.5 mL) and ethanol (0.3 mL), sodium borohydride (1.2 mg, 0.032 mmol) was added at room temperature, and the resulting mixture was stirred at the same temperature for 30 minutes. 1 M hydrochloric acid was added to the reaction mixture, and the resulting mixture was extracted with ethyl acetate. The organic layer was concentrated under reduced pressure to obtain the title compound (2.0 mg, 39% yield).

$^1$H-NMR Spectrum (400 MHz, CDCl$_3$) δ (ppm): 4.77 (s, 2H), 4.93 (t, J=4.0 Hz, 2H), 5.06 (t, J=4.0 Hz, 2H), 6.76 (s, 1H).

Example 6

2-Amino-5,7-dihydrofuro[3,4-b]pyrazine

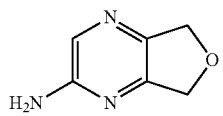

A mixture of 2-amino-5-bromo-6-chloro-pyrazine (21 mg, 0.10 mmol), tributyl{[(tributylstannyl)methoxy]

methyl}stannane according to Production Example 1-2 (62 mg, 0.10 mmol), tris(dibenzylideneacetone)dipalladium (9.2 mg, 0.010 mmol), X-Phos (19 mg, 0.040 mmol), and 1,4-dioxane (1.0 mL) was stirred while being heated to reflux for 20 hours. The resulting mixture was cooled to room temperature and then filtered through Celite and concentrated under reduced pressure. The residue was separated and purified by preparative thin-layer chromatography (ethyl acetate:heptane=5:1) to obtain the title compound (3.6 mg, 26% yield).

$^1$H-NMR Spectrum (400 MHz, CDCl$_3$) δ (ppm): 4.55 (br s, 2H), 4.87-5.13 (m, 4H), 7.83 (s, 1H).

Example 7

2-Amino-5,7-dihydrofuro[3,4-b]pyridine

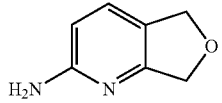

6-Amino-2,3-dibromopyridine (25 mg, 0.10 mmol), tributyl{[(tributylstannyl)methoxy]methyl}stannane according to Production Example 1-2 (62 mg, 0.10 mmol), tris(dibenzylideneacetone)dipalladium (9.2 mg, 0.010 mmol), X-Phos (19 mg, 0.040 mmol), and 1,4-dioxane (1.0 mL) were stirred while being heated to reflux for 20 hours. The resulting mixture was cooled to room temperature and then filtered through Celite and concentrated under reduced pressure. The residue was separated and purified by preparative thin-layer chromatography (ethyl acetate:heptane=5:1) to obtain the title compound (3.4 mg, 25% yield).

$^1$H-NMR Spectrum (400 MHz, CDCl$_3$) δ (ppm): 4.44 (br s, 2H), 4.80-5.18 (m, 4H), 6.38 (d, J=8.1 Hz, 1H), 7.31 (d, J=8.4 Hz, 1H).

Example 8

Methyl 4,6-dihydro-1H-furo[3,4-b]pyrrole-2-carboxylate

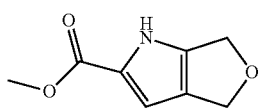

Methyl 4,5-dibromo-1H-pyrrole-2-carboxylate (27 mg, 0.10 mmol), tributyl{[(tributylstannyl)methoxy]methyl}stannane according to Production Example 1-2 (62 mg, 0.10 mmol), tris(dibenzylideneacetone)dipalladium (9.2 mg, 0.010 mmol), X-Phos (19 mg, 0.040 mmol), and 1,4-dioxane (1.0 mL) were stirred while being heated to reflux for 17 hours. The resulting mixture was cooled to room temperature and then filtered through Celite and concentrated under reduced pressure. The residue was separated and purified by preparative thin-layer chromatography (ethyl acetate:heptane=3:1) to obtain the title compound (2.6 mg, 17% yield).

$^1$H-NMR Spectrum (400 MHz, CDCl$_3$) δ (ppm): 3.85 (s, 3H), 4.89 (s, 4H), 6.69 (d, J=1.5 Hz, 1H), 8.98 (br s, 1H).

Example 9 tert-Butyl N-[(tert-butoxy)carbonyl]-N-{1,3-dihydrofuro[3,4-c]pyridin-6-yl}carbamate

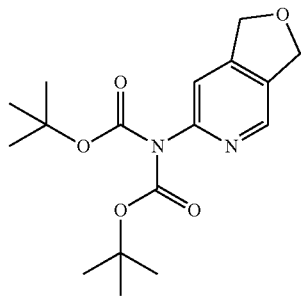

mixture of tert-butyl N-[(tert-butoxy)carbonyl]-N-(4,5-dichloropyridin-2-yl)carbamate according to Production Example 9-1 (36 mg, 0.10 mmol), tributyl{[(tributylstannyl)methoxy]methyl}stannane according to Production Example 1-2 (62 mg, 0.10 mmol), tris(dibenzylideneacetone)dipalladium (9.2 mg, 0.010 mmol), X-Phos (19 mg, 0.040 mmol), and 1,4-dioxane (1.0 mL) was stirred while being heated to reflux for 14 hours. The reaction mixture was cooled to room temperature and then filtered through Celite and concentrated under reduced pressure. The residue was separated and purified by preparative thin-layer chromatography (ethyl acetate:heptane=1:2) to obtain the title compound (11 mg, 32% yield).

$^1$H-NMR Spectrum (400 MHz, CDCl$_3$) δ (ppm): 1.47 (s, 18H), 5.10 (s, 2H), 5.15 (s, 2H), 7.16 (d, J=0.73 Hz, 1H), 8.38 (d, J=0.73 Hz, 1H).

Production Example 9-1 tert-Butyl N-[(tert-butoxy)carbonyl]-N-(4,5-dichloropyridin-2-yl)carbamate

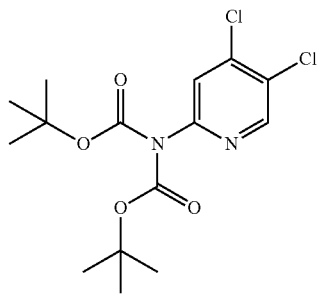 [SMILES: CC(C)(C)OC(=O)N(C(=O)OC(C)(C)C)c1cc(Cl)c(Cl)cn1]

To a solution of 2-amino-4,5-dichloropyridine (0.10 g, 0.61 mmol) and diisopropylethylamine (0.26 mL, 1.5 mmol) in dichloromethane (10 mL), di-tert-butyldicarbonate (0.32 g, 1.5 mmol) was added, and the resulting mixture was stirred at room temperature overnight. Water was added to the reaction mixture, and the resulting mixture was extracted with ethyl acetate. The organic layer was washed with a saturated saline solution and dried over anhydrous magnesium sulfate. The solvent was concentrated under reduced pressure, and then the residue was separated and purified by silica gel column chromatography (ethyl acetate:heptane=1:5) to obtain the title compound (0.18 g, 80% yield).

¹H-NMR Spectrum (400 MHz, CDCl₃) δ (ppm): 1.48 (s, 18H), 7.46 (s, 1H), 8.46 (s, 1H).

Example 10

Methyl 4,6-dihydrofuro[3,4-d]isothiazole-3-carboxylate

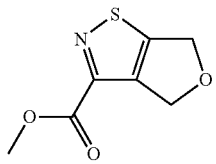

A mixture of methyl 4,5-dichloro-isothiazole-3-carboxylate according to Production Example 10-1 (21 mg, 0.10 mmol), tributyl{[tributylstannyl)methoxy]methyl}stannane according to Production Example 1-2 (62 mg, 0.10 mmol), tris(dibenzylideneacetone)dipalladium (9.2 mg, 0.010 mmol), X-Phos (19 mg, 0.040 mmol), and 1,4-dioxane (1.0 mL) was stirred while being heated to reflux for 14 hours. The reaction mixture was cooled to room temperature and then filtered through Celite, and the filtrate was concentrated under reduced pressure. The residue was separated and purified by preparative thin-layer chromatography (ethyl acetate:heptane=3:1) to obtain the title compound (1.6 mg, 8.6% yield).

¹H-NMR Spectrum (400 MHz, CDCl₃) δ (ppm): 3.97 (s, 3H), 5.18 (dd, J=2.9, 9.5 Hz, 4H).

Production Example 10-1

Methyl 4,5-dichloro-isothiazole-3-carboxylate

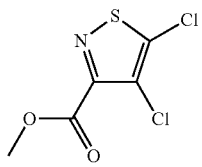

To a mixed solution of 4,5-dichloroisothiazole-3-carboxylic acid (0.20 g, 1.0 mmol) in tetrohydrofuran (5.0 mL) and methanol (0.50 mL), trimethylsilyldiazomethane (0.76 mL, 1.5 mmol, a 2.0 M solution in tetrahydrofuran) was added dropwise at 0° C. The resulting mixture was then stirred at room temperature for 10 minutes, and then a mixture of acetic acid and water (1:1) (0.18 mL) was added dropwise thereto at 0° C., and the reaction mixture was stirred for 30 minutes. Water was added to the reaction mixture, and the resulting mixture was extracted with ethyl acetate. The organic layer was washed with a saturated saline solution, and then dried over anhydrous magnesium sulfate. The solvent was concentrated under reduced pressure, and then the residue was separated and purified by silica gel column chromatography (ethyl acetate:heptane=1:10) to obtain the title compound (0.18 g, 85% yield).

¹H-NMR Spectrum (400 MHz, CDCl₃) δ (ppm): 4.01 (s, 3H).

Example 11

Methyl 3-amino-5,7-dihydrofuro[3,4-b]pyrazine-2-carboxylate

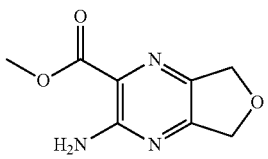

A mixture of methyl 3-amino-5,6-dichloropyrazine-2-carboxylate (20 mg, 0.090 mmol), tributyl{[(tributylstannyl)methoxy]methyl}stannane according to Production Example 1-2 (56 mg, 0.090 mmol), tris(dibenzylideneacetone)dipalladium (8.2 mg, 0.0090 mmol), X-Phos (26 mg, 0.054 mmol), and 1,4-dioxane (0.90 mL) was stirred for 14 hours while being heated to reflux. The resulting mixture was cooled to room temperature, filtered through Celite, and concentrated under reduced pressure. The residue was separated and purified by preparative thin-layer chromatography (ethyl acetate:heptane=5:1) to obtain the title compound (8.9 mg, 51% yield).

¹H-NMR Spectrum (400 MHz, CDCl₃) δ (ppm): 4.00 (s, 3H), 4.92-5.09 (m, 4H).

Example 12

Methyl 3-hydroxy-4,6-dihydrothieno[2,3-c]furan-2-carboxylate

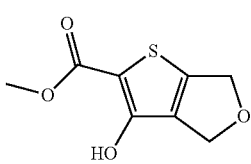

A mixture of methyl 4,5-dibromo-3-hydroxythiophene-2-carboxylate (38 mg, 0.12 mmol), tributyl{[tributylstannyl)methoxy]methyl}stannane according to Production Example 1-2 (75 mg, 0.12 mmol), palladium acetate (2.7 mg, 0.012 mmol), X-Phos (12 mg, 0.025 mmol), and 1,4-dioxane (1.2 mL) was stirred for 14 hours while being heated to reflux. The resulting mixture was cooled to room temperature, filtered through Celite, and concentrated under reduced pressure. The residue was separated and purified by preparative thin-layer chromatography (ethyl acetate:heptane=1:5) to obtain the title compound (11 mg, 44% yield).

¹H-NMR Spectrum (400 MHz, CDCl₃) δ (ppm): 3.89 (s, 3H), 4.87-5.11 (m, 4H).

Example 13

2-Chloro-4,6-dihydrothieno[2,3-c]furan

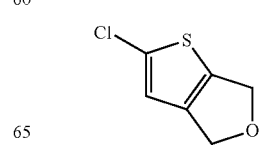

To a reaction mixture of 3-bromo-2,5-dichloro thiophene (23 mg, 0.10 mmol), tributyl{[(tributylstannyl)methoxy]methyl}stannane according to Production Example 1-2 (62 mg, 0.10 mmol), tris(dibenzylideneacetone)dipalladium (9.2 mg, 0.010 mmol), and X-Phos (19 mg, 0.040 mmol), 1,4-dioxane (1 mL) was added thereto, and the resulting mixture was stirred for 15 hours while being heated to reflux. The resulting mixture was cooled to room temperature, dichloromethane (1 mL) and a saturated aqueous solution of potassium fluoride (0.1 mL) were added thereto, and the resulting mixture was stirred at room temperature for 1 hour. The reaction mixture was filtered through Celite, water was added to the filtrate, and the resulting mixture was extracted with diethyl ether. The organic layer was washed with a saturated saline solution, and the solvent was distilled off under reduced pressure. The residue was purified by silica gel column chromatography (diethyl ether:hexane=1:15) to obtain the title compound (2.1 mg, 13% yield). The product was identified by GC-MS.

MS(EI) m/z 159.97 (M+•)

Example 14

4-Amino-5,7-dihydrofuro[3,4-d]pyrimidine

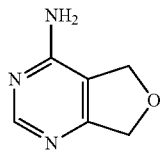

To a mixture of 5-bromo-6-chloropyrimidin-4-amine (15 mg, 0.070 mmol), tributyl{[tributylstannyl)methoxy]methyl}stannane according to Production Example 1-1 (53 mg, 0.084 mmol), tris(dibenzylideneacetone)dipalladium (6.4 mg, 0.0070 mmol), and X-Phos (13 mg, 0.028 mmol), 1,4-dioxane (0.7 mL) was added, and the resulting mixture was stirred at 135° C. for 2 hours under microwave irradiation. The resulting mixture was cooled to room temperature, and then concentrated under reduced pressure. The residue was purified by preparative thin-layer chromatography (ethyl acetate:methanol=20:1) to obtain the title compound (2.4 mg, 25% yield).

MS(ESI) m/z 138(MH)$^+$

Example 15

1-Bromo-5,7-dihydrofuro[3,4-d]pyridazine

A mixture of 2,3,4,6-tetrahydro-2H-furo[3,4-d]pyridazin-3-one according to Example 1 (10 mg, 0.072 mmol) and phosphorus tribromide (0.3 mL) was stirred at 130° C. for 30 minutes. The reaction mixture was poured onto ice, and a 5 N aqueous solution of sodium hydroxide was added dropwise to the reaction mixture under ice cooling for neutralization. Water and ethyl acetate were added to the reaction mixture for extraction. The organic layer was washed with a saturated saline solution, and the solvent was distilled off under reduced pressure. The residue was purified by silica gel column chromatography (ethyl acetate:heptane=3:2) to obtain the title compound (1.3 mg, 9% yield) as a mixture with a byproduct 3-bromo-4,5-dimethylpyridazine.

$^1$H-NMR Spectrum (400 MHz, CDCl$_3$) δ (ppm): 5.12-5.16 (m, 2H), 5.26-5.30 (m, 2H), 9.16 (s, 1H).

MS (ESI) m/z 201 (MH)$^+$ and 203 (MH)$^+$

Reference Example 1

2,6-Diamino-N-[(4-{1,3-dihydrothieno[2,3-c]furan-2-ylmethyl}phenyl)methyl]pyridine-3-carboxamide

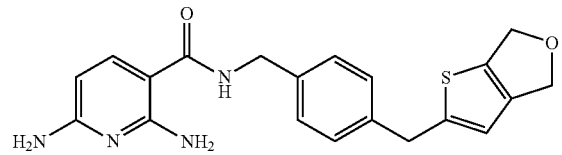 [SMILES: Nc1ccc(C(=O)NCc2ccc(Cc3cc4c(s3)COC4)cc2)c(N)n1]

To a mixture of (4-{1,3-dihydrothieno[2,3-c]furan-2-ylmethyl}phenyl)methylamine according to Production Example 16-2 (5.1 mg, 0.0082 mmol) and dimethylsulfoxide (1 mL), triethylamine (3.4 μL, 0.025 mmol), 2,6-diaminonicotinic acid (1.3 mg, 0.0082 mmol), 1-hydroxybenzotriazole (1.7 mg, 0.012 mmol), and 1-ethyl-3-(3-dimethylaminopropyl)carbodiimide hydrochloride (2.4 mg, 0.012 mmol) were sequentially added at room temperature, and the resulting mixture was stirred at room temperature for 3 days. Water was added to the reaction mixture, and the resulting mixture was extracted with dichloromethane. The organic layer was washed with a saturated saline solution, and the solvent was distilled off under reduced pressure. The residue was purified by preparative thin-layer chromatography (ethyl acetate:methanol=50:1) to obtain the title compound (0.80 mg, 26% yield).

$^1$H-NMR Spectrum (400 MHz, CDCl$_3$) δ (ppm): 4.10 (s, 2H), 4.54 (d, J=5.5 Hz, 4H), 4.88-4.92 (m, 2H), 5.00-5.03 (m, 2H), 5.77 (d, J=8.4 Hz, 1H), 6.02 (br s, 1H), 6.47 (br s, 2H), 6.54 (s, 1H), 7.22-7.26 (m, 2H), 7.27-7.31 (m, 2H), 7.38 (d, J=8.4 Hz, 1H).

Production Example 16-1

(1,3-Dihydrothieno[2,3-c]furan-5-yl)(4-cyanophenyl)methanol

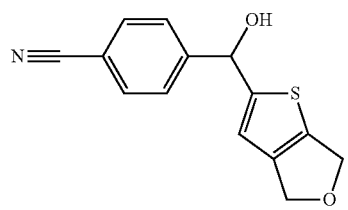 [SMILES: N#Cc1ccc(C(O)c2cc3c(s2)COC3)cc1]

To a mixture of 4-iodobenzonitrile (130 mg, 0.55 mmol), and tetrahydrofuran (1.5 mL), isopropylmagnesium chloride (a 2.0 M solution in tetrahydrofuran, 0.24 mL, 0.48 mmol) was added dropwise under ice cooling, and the resulting mixture was stirred at the same temperature for 30 minutes. 4,6-Dihydrothieno[2,3-c]furan-2-carbaldehyde according to Example 4 (67 mg, 0.44 mmol) was added to the reaction mixture under ice cooling, and the resulting mixture was stirred at the same temperature for 30 minutes. An aqueous solution of ammonium chloride was added to the reaction mixture at the same temperature, and the resulting mixture was extracted with ethyl acetate. The organic layer was washed with a saturated saline solution, and the solvent was distilled off under reduced pressure. The residue was purified by NH-silica gel column chromatography (ethyl acetate: heptane=1:2) to obtain the title compound (9.0 mg, 8.0% yield). $^1$H-NMR Spectrum (400 MHz, CDCl$_3$) δ (ppm): 2.64 (d, J=3.7 Hz, 1H), 4.88-4.91 (m, 2H), 5.02-5.05 (m, 2H), 6.05 (d, J=3.7 Hz, 1H), 6.66 (s, 1H), 7.57-7.61 (m, 2H), 7.64-7.69 (m, 2H).

Production Example 16-2

(4-{1,3-Dihydrothieno[2,3-c]furan-2-ylmethy}phenyl)methylamine

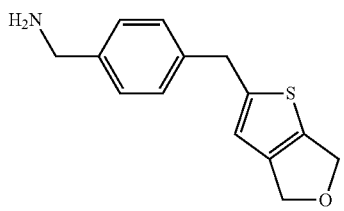 [SMILES: NCc1ccc(Cc2cc3c(s2)COC3)cc1]

To a mixture of lithium aluminum hydride (8.0 mg, 0.21 mmol), and tetrahydrofuran (0.66 mL), aluminum chloride (37 mg, 0.28 mmol) was added under ice cooling, and the resulting mixture was stirred at room temperature for 1 hour. A mixture of (1,3-dihydrothieno[2,3-c]furan-5-yl)(4-cyanophenyl)methanol according to Production Example 16-1 (9.0 mg, 0.035 mmol), and tetrahydrofuran (0.33 mL) was added dropwise to the reaction mixture under ice cooling, and the resulting mixture was stirred at room temperature for 2 hours. An aqueous solution of ammonia was added to the reaction mixture under ice cooling, the resulting mixture was stirred at room temperature for 30 minutes and then filtered through Celite. The solvent in the filtrate was distilled off under reduced pressure, and the residue was filtered by using NH-silica gel (ethyl acetate:methanol=10:1). The title compound was obtained as a crude material. The obtained compound was used for a next reaction without further purification.

Reference Example 2

5-Amino-N-({4-[(pyridin-2-yloxy)methyl]phenyl}methyl)-1,3-dihydrofuro[3,4-b]pyrazine-6-carboxamide

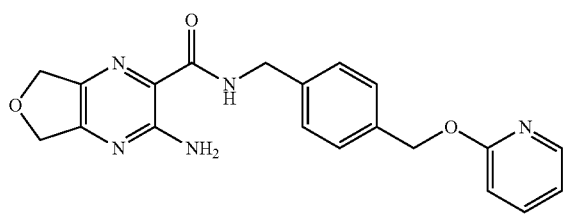 [SMILES: Nc1nc2c(nc1C(=O)NCc1ccc(COc3ccccn3)cc1)COC2]

To a mixture of lithium 3-amino-5,7-dihydrofuro[3,4-b]pyrazine-2-carboxylate according to Example 16 (6.0 mg, 0.032 mmol) and N,N-dimethylformamide (1 mL), 4-(pyridin-2-yloxymethyl)-benzylamine according to WO 2005/033079 (6.9 mg, 0.032 mmol), HATU(O-(7-azabenzotriazol-1-yl)-N,N,N',N'-tetramethyluronium hexafluorophosphate) (18 mg, 0.048 mmol), and N,N-diisopropylethylamine (8.2 µL, 0.048 mmol) were sequentially added at room temperature, and the resulting mixture was stirred at room temperature for 3 days. Water was added to the reaction mixture, and the resulting mixture was extracted with ethyl acetate. The organic layer was washed with a saturated saline solution, and the solvent was distilled off under reduced pressure. The residue was purified by silica gel column chromatography (ethyl acetate:heptane=1:1) to obtain the title compound (7.0 mg, 58% yield).
$^1$H-NMR Spectrum (400 MHz, DMSO-d$_6$) δ (ppm): 4.43 (d, J=6.2 Hz, 2H), 4.88 (s, 2H), 4.90 (s, 2H), 5.30 (s, 2H), 6.84 (d, J=8.1 Hz, 1H), 6.96-7.00 (m, 1H), 7.29-7.33 (m, 2H), 7.36-7.40 (m, 2H), 7.48-7.79 (m, 3H), 8.15-8.18 (m, 1H), 9.24 (t, J=6.2 Hz, 1H).

Example 16

Lithium 3-amino-5,7-dihydrofuro[3,4-b]pyrazine-2-carboxylate

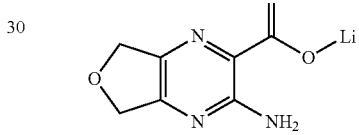

To a mixture of methyl 3-amino-5,7-dihydrofuro[3,4-b]pyrazine-2-carboxylate according to Example 11 (24 mg, 0.12 mmol), tetrahydrofuran (1 mL), methanol (0.25 mL) and water (0.25 mL), lithium hydroxide monohydrate (5.2 mg, 0.12 mmol) was added at room temperature, and the resulting mixture was stirred at room temperature overnight. The solvent was distilled off from the reaction mixture under reduced pressure to obtain the title compound (23 mg).
$^1$H-NMR Spectrum (400 MHz, DMSO-d$_6$) δ (ppm): 4.81 (s, 4H).

Comparative Example 1

2,6-Diamino-N-({4-[(4,5-dimethylthiophen-2-yl)methyl]phenyl}methyl)-pyridine-3-carboxamide

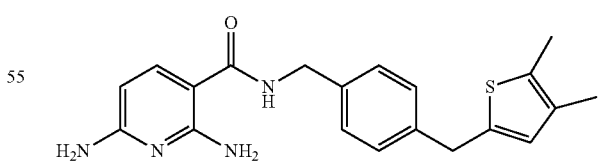

To a mixture of 14-[(4,5-dimethylthiophen-2-yl)methyl]phenyllmethylamine according to Production Example 17-2 (42 mg, 0.18 mmol) and dimethylsulfoxide (1.5 mL), triethylamine (76 µL, 0.55 mmol), 2,6-diaminonicotinic acid (28 mg, 0.18 mmol), 1-hydroxybenzotriazole (37 mg, 0.27 mmol), and 1-ethyl-3-(3-dimethylaminopropyl)carbodiimide hydrochloride (52 mg, 0.27 mmol) were sequentially added at room temperature, and the resulting mixture was stirred at room temperature overnight. Water was added to the reaction mixture, and the resulting mixture was extracted with dichloromethane. The organic layer was washed with a saturated saline solution, and the solvent was distilled off under reduced pressure. The residue was purified by silica gel column chromatography (ethyl acetate:methanol=50:1) to obtain the title compound (27 mg, 40% yield).

$^1$H-NMR Spectrum (400 MHz, DMSO-$d_6$) δ (ppm): 1.99 (s, 3H), 2.19 (s, 3H), 3.94 (s, 2H), 4.33 (d, J=5.9 Hz, 2H), 5.67 (d, J=8.4 Hz, 1H), 6.07 (br s, 2H), 6.52 (s, 1H), 6.94 (br s, 2H), 7.17 (q, J=8.4 Hz, 4H), 7.66 (d, J=8.4 Hz, 1H), 8.31 (t, J=5.9 Hz, 1H).

Production Example 17-1

(4,5-Dimethylthiophen-2-yl)(4-cyanophenyl)methanol

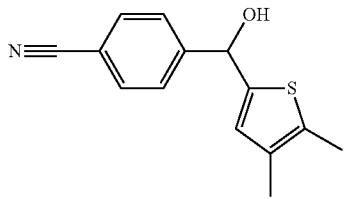 [SMILES: Cc1cc(C(O)c2ccc(C#N)cc2)sc1C]

To a mixture of 4-iodobenzonitrile (100 mg, 0.44 mmol), and tetrahydrofuran (1.5 mL), isopropylmagnesium chloride (a 2.0 M solution in tetrahydrofuran, 0.24 mL, 0.48 mmol) was added dropwise under ice cooling, and the resulting mixture was stirred at room temperature for 30 minutes. 4,5-Dimethylthiophene-2-carbaldehyde (61 mg, 0.44 mmol) was added to the reaction mixture under ice cooling, and the resulting mixture was stirred at the same temperature for 30 minutes. An aqueous solution of ammonium chloride was added to the reaction mixture at the same temperature, and the resulting mixture was extracted with ethyl acetate. The organic layer was washed with a saturated saline solution, and the solvent was distilled off under reduced pressure. The residue was purified by NH-silica gel column chromatography (ethyl acetate:heptane=1:2) to obtain the title compound (44 mg, 41% yield).

$^1$H-NMR Spectrum (400 MHz, DMSO-$d_6$) δ (ppm): 2.06 (s, 3H), 2.29 (s, 3H), 2.34 (d, J=3.7 Hz, 1H), 5.98 (d, J=3.7 Hz, 1H), 6.61 (s, 1H), 7.55-7.58 (m, 2H), 7.63-7.67 (m, 2H).

Production Example 17-2

{4-[(4,5-Dimethylthiophen-2-yl)methyl]phenyl}methylamine

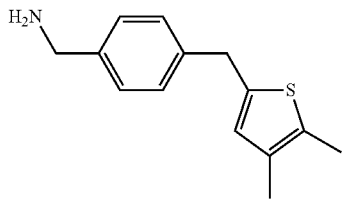 [SMILES: Cc1cc(Cc2ccc(CN)cc2)sc1C]

To a mixture of lithium aluminum hydride (26 mg, 0.69 mmol), and tetrahydrofuran (2 mL), aluminum chloride (120 mg, 0.92 mmol) was added under ice cooling, and the resulting mixture was stirred at room temperature for 1 hour. A mixture of (4,5-dimethylthiophen-2-yl)(4-cyanophenyl)methanol according to Production Example 17-1 (28 mg, 0.12 mmol), and tetrahydrofuran (1 mL) was added dropwise to the reaction mixture under ice cooling, and the resulting mixture was stirred at room temperature for 1 hour. An aqueous solution of ammonia was added to the reaction mixture under ice cooling, the resulting mixture was stirred at room temperature for 30 minutes, and then filtered through Celite. The solvent in the filtrate was distilled off under reduced pressure, and the residue was filtered by using NH-silica gel (ethyl acetate:methanol=10:1). The title compound was obtained as a crude material. The obtained compound was used for a next reaction without further purification.

Comparative Example 2

3-Amino-5,6-dimethyl-N-({4-[(pyridin-2-yloxy)methyl]phenyl}methyl)pyrazine-2-carboxamide

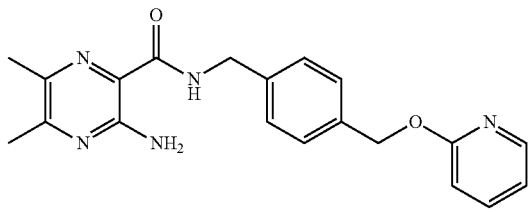 [SMILES: Cc1nc(N)c(C(=O)NCc2ccc(COc3ccccn3)cc2)nc1C]

To a mixture of lithium 3-amino-5,6-dimethylpyrazine-2-carboxylate according to Production Example 18-2 (6.5 mg, 0.038 mmol) and N,N-dimethylformamide (1 mL), 4-(pyridin-2-yloxymethyl)-benzylamine according to WO 2005/033079 (8.1 mg, 0.038 mmol), HATU(O-(7-azabenzotriazol-1-yl)-N,N,N',N'-tetramethyluronium hexafluorophosphate) (21 mg, 0.056 mmol), and N,N-diisopropylethylamine (9.6 µL, 0.056 mmol) were sequentially added at room temperature, and the resulting mixture was stirred at room temperature for 3 days. Water was added to the reaction mixture, and the resulting mixture was extracted with ethyl acetate. The organic layer was washed with a saturated saline solution, and the solvent was distilled off under reduced pressure. The residue was purified by silica gel column chromatography (ethyl acetate:heptane=1:1) to obtain the title compound (3.0 mg, 22% yield).

$^1$H-NMR Spectrum (400 MHz, DMSO-$d_6$) δ (ppm): 2.34 (s, 6H), 4.45 (d, J=6.2 Hz, 2H), 5.31 (s, 2H), 6.85 (d, J=8.4 Hz, 1H), 6.96-7.00 (m, 1H), 7.19 (br s, 2H), 7.28-7.33 (m, 2H), 7.36-7.41 (m, 2H), 7.71 (ddd, J=8.6, 7.0, 2.0 Hz, 1H), 8.16 (dd, J=5.1, 1.8 Hz, 1H), 9.00 (t, J=6.4 Hz, 1H).

Production Example 18-1

Methyl 3-amino-5,6-dimethylpyrazine-2-carboxylate

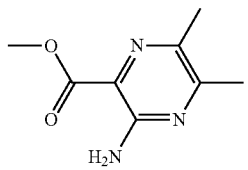

A mixture of methyl 3-amino-5,6-dichloro-2-pyrazine carboxylate (200 mg, 0.90 mmol), X-Phos (170 mg, 0.36 mmol), tris(dibenzylideneacetone)dipalladium(0) (82 mg, 0.090 mmol), tetramethyltin (0.31 mL, 2.3 mmol), and N-methylpyrrolidinone (2 mL) was stirred at 130° C. for 2 hours under microwave irradiation. The reaction mixture was cooled to room temperature, water was added thereto at the same temperature, and the resulting mixture was extracted with ethyl acetate. The organic layer was washed with a saturated saline solution, and the solvent was distilled off under reduced pressure. The residue was purified by silica gel column chromatography (ethyl acetate:heptane=3:2) to obtain the title compound (80 mg, 49% yield).

$^1$H-NMR Spectrum (400 MHz, CDCl$_3$) δ (ppm): 2.44 (s, 3H), 2.46 (s, 3H), 3.97 (s, 3H), 6.22 (br s, 2H).

Production Example 18-2

Lithium 3-amino-5,6-dimethylpyrazine-2-carboxylate

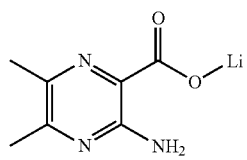

To a mixture of methyl 3-amino-5,6-dimethylpyrazine-2-carboxylate according to Production Example 18-1 (71 mg, 0.39 mmol), tetrahydrofuran (1 mL), methanol (0.25 mL), and water (0.25 mL), lithium hydroxide monohydrate (17 mg, 0.41 mmol) was added at room temperature, and the resulting mixture was stirred at room temperature overnight. Tetrahydrofuran (2 mL) was added to the reaction mixture at room temperature, and the solid was filtered off to obtain the title compound (63 mg, 93% yield).

$^1$H-NMR Spectrum (400 MHz, DMSO-d$_6$) δ (ppm): 2.21 (s, 3H), 2.28 (s, 3H).

Example 19

3-Chloro-5,7-dihydrofuro[3,4-b]pyridine

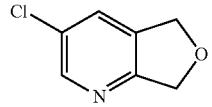

A mixture of 2,3,5-trichloro pyridine (200 mg, 1.1 mmol), tributyl({[(tributylstannyl)methoxy]methyl})stannane according to Production Example 1-2 (680 mg, 1.1 mmol), tris(dibenzylideneacetone)dipalladium (100 mg, 0.11 mmol), X-Phos (120 mg, 0.24 mmol), and 1,4-dioxane (11 mL) was stirred for 18 hours while being heated to reflux. The reaction mixture was cooled to room temperature and then filtered through Celite, and the obtained filtrate was concentrated under reduced pressure. The residue was purified roughly by silica gel column chromatography (ethyl acetate:heptane=0:100-15:85, gradient), and then the obtained roughly purified product was separated and purified by NH-silica gel column chromatography (ethyl acetate:heptane=0:100-12:88, gradient) to obtain the title compound (30 mg, 18% yield).

$^1$H-NMR Spectrum (400 MHz, CDCl$_3$) δ (ppm): 5.02-5.05 (m, 2H), 5.13-5.17 (m, 2H), 7.54 (d, J=1.2 Hz, 1H), 8.42-8.46 (m, 1H).

Example 20

3-(4,4,5,5-Tetramethyl-1,3,2-dioxaborolan-2-yl)-5,7-dihydrofuro[3,4-b]pyridine

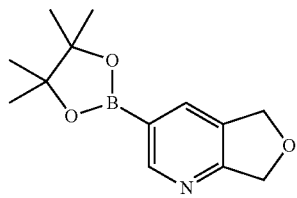 [SMILES: CC1(C)OB(c2cnc3c(c2)COC3)OC1(C)C]

A mixture of tris(dibenzylideneacetone)dipalladium (5.9 mg, 0.0064 mmol), tricyclohexylphosphine (4.0 mg, 0.014 mmol), and 1,4-dioxane (1 mL) was stirred at room temperature for 15 minutes. 3-Chloro-5,7-dihydrofuro[3,4-b]pyridine according to Example 19 (10 mg, 0.064 mmol), bispinacolate diboron (20 mg, 0.077 mmol), and potassium acetate (19 mg, 0.19 mmol) were added to the mixture, and the resulting mixture was stirred for 18 hours while being heated to reflux. The reaction mixture was cooled to room temperature and then filtered through Celite, and the obtained filtrate was concentrated under reduced pressure. The residue was separated and purified by preparative LCMS (mobile phase: acetonitrile/water, 0.1% acetic acid) to obtain the title compound (9 mg, 57% yield).

$^1$H-NMR Spectrum (400 MHz, CDCl$_3$) δ (ppm): 1.36 (s, 12H), 5.09 (t, J=2.0 Hz, 2H), 5.16 (br s, 2H), 7.94 (s, 1H), 8.83 (s, 1H).

Example 21

3-(Tributylstannyl)-5,7-dihydrofuro[3,4-b]pyridine

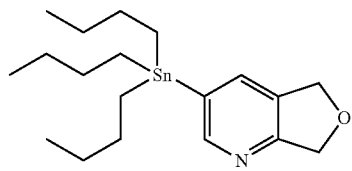 [SMILES: CCC[CH2][Sn]([CH2]CCC)([CH2]CCC)[c]1cnc2c(c1)COC2]

3-Chloro-5,7-dihydrofuro[3,4-b]pyridine according to Example 19 (50 mg, 0.32 mmol), hexa-(n-butyl)ditin (620 mg, 0.96 mmol), tetrakis(triphenylphosphine)palladium(0) (37 mg, 0.032 mmol), lithium chloride (68 mg, 1.6 mmol), and 1,4-dioxane (3 mL) were mixed, and the obtained mixture was stirred at 160° C. for 1 hour under microwave irradiation. The reaction mixture was cooled to room temperature and then filtered through Celite, and concentrated under reduced pressure. The residue was purified by preparative LCMS (mobile phase: acetonitrile/water, 0.1% acetic acid), and then the obtained roughly purified product was separated and purified by silica gel column chromatography (ethyl acetate:heptane=0:100-29:71, gradient) to obtain the title compound (10 mg, 7.6% yield).

¹H-NMR Spectrum (400 MHz, CDCl₃) δ (ppm): 0.84-0.95 (m, 9H), 1.02-1.20 (m, 6H), 1.27-1.40 (m, 6H), 1.43-1.63 (m, 6H), 5.05-5.10 (m, 2H), 5.17 (d, J=0.78 Hz, 2H), 7.63 (d, J=0.78 Hz, 1H), 8.45 (s, 1H).

Example 22

Methyl 5,7-dihydrofuro[3,4-b]pyridine-3-carboxylate

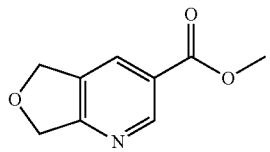

Methyl 5,6-dichloropyridine-3-carboxylate (300 mg, 1.5 mmol), tributyl({[(tributylstannyl)methoxy]methyl})stannane according to Production Example 1-2 (910 mg, 1.5 mmol), tris(dibenzylideneacetone)dipalladium (130 mg, 0.15 mmol), X-Phos (150 mg, 0.32 mmol), and 1,4-dioxane (15 mL) were mixed, and the resulting mixture was stirred for 22 hours while being heated to reflux. The reaction mixture was cooled to room temperature, then an aqueous solution of potassium fluoride was added thereto, and the resulting mixture was stirred. The reaction mixture was filtered through Celite, and the filtrate was concentrated under reduced pressure. The residue was purified by NH-silica gel column chromatography (ethyl acetate:heptane=1:99-24:76, gradient), and then the obtained roughly purified product was separated and purified by silica gel column chromatography (ethyl acetate:heptane=15:85-52:48, gradient) to obtain the title compound (120 mg, 48% yield).

¹H-NMR Spectrum (400 MHz, CDCl₃) δ (ppm): 3.96 (s, 3H), 5.12 (t, J=1.8 Hz, 2H), 5.19-5.22 (m, 2H), 8.16 (d, J=1.2 Hz, 1H), 9.12 (d, J=1.2 Hz, 1H).

Example 23 tert-Butyl N-[(tert-butoxy)carbonyl]-N-{1,3-dihydrofuro[3,4-c]pyridin-6-yl}carbamate

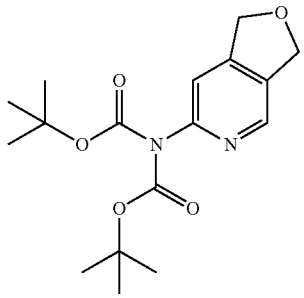 [SMILES: CC(C)(C)OC(=O)N(C(=O)OC(C)(C)C)c1cc2c(cn1)COC2]

tert-Butyl N-(5-bromo-4-chloropyridin-2-yl)-N-[(tert-butoxy)carbonyl]carbamate according to Production Example 23-1 (1.0 g, 2.5 mmol), tributyl(I[(tributylstannyl)methoxy]methylpstannane according to Production Example 1-2 (1.5 g, 2.5 mmol), tris(dibenzylideneacetone)dipalladium (230 mg, 0.25 mmol), X-Phos (260 mg, 0.54 mmol), and 1,4-dioxane (24 mL) were mixed, and the resulting mixture was stirred for 22 hours while being heated to reflux. The reaction mixture was cooled to room temperature and then filtered through Celite, and concentrated under reduced pressure. The residue was purified by silica gel column chromatography (ethyl acetate:heptane=0:100-23:77, gradient), and then the roughly purified product was purified again by NH-silica gel column chromatography (ethyl acetate:heptane=1:99-18:82, gradient). The obtained roughly purified product was separated and purified by silica gel column chromatography (ethyl acetate:heptane=0:100-30:70, gradient) to obtain the title compound (360 mg, 44% yield).

¹H-NMR Spectrum (400 MHz, CDCl₃) δ (ppm): 1.48 (s, 18H), 5.12 (s, 2H), 5.16 (s, 2H), 7.17 (s, 1H), 8.40 (s, 1H).

Production Example 23-1 tert-Butyl N-(5-bromo-4-chloropyridin-2-yl)-N-[(tert-butoxy)carbonyl]carbamate

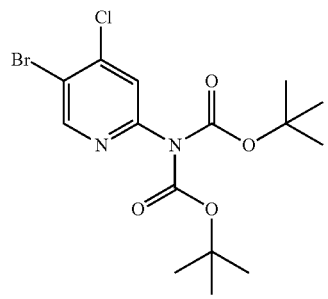 [SMILES: CC(C)(C)OC(=O)N(C(=O)OC(C)(C)C)c1cc(Cl)c(Br)cn1]

To a solution of 5-bromo-4-chloropyridin-2-amine (3.0 g, 14 mmol), di-tert-butyl dicarbonate (9.5 g, 43 mmol), and triethylamine (6.1 mL, 43 mmol) in tetrahydrofuran (100 mL), 4-dimethylaminopyridine (0.18 g, 1.5 mmol) was added, and the resulting mixture was stirred at room temperature overnight. The reaction mixture was concentrated under reduced pressure, and then the residue was separated and purified by silica gel column chromatography (ethyl acetate:heptane) to obtain the title compound (3.2 g, 55% yield). ¹H-NMR Spectrum (400 MHz, CDCl₃) δ (ppm): 1.48 (s, 18H), 7.47 (s, 1H), 8.58 (s, 1H).

Example 24

1,3-Dihydrofuro[3,4-c]pyridin-6-amine

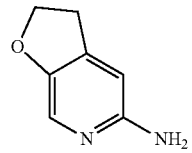

To a solution of tert-butyl N-[(tert-butoxy)carbonyl]-N-{1,3-dihydrofuro[3,4-c]pyridin-6-yl}carbamate according to Example 23 (360 mg, 1.1 mmol) in dichloromethane (6 mL), trifluoroacetic acid (2 mL, 26 mmol) was added, and the resulting mixture was stirred at room temperature overnight. Toluene was added to the reaction liquid, and the resulting mixture was concentrated under reduced pressure. The residue was separated and purified by NH-silica gel column chromatography (ethyl acetate:heptane=50:50-100:0, gradient) to obtain the title compound (130 mg, 89% yield).

¹H-NMR Spectrum (400 MHz, CDCl₃) δ (ppm): 4.43 (br s, 2H), 4.95-4.99 (m, 2H), 5.01-5.05 (m, 2H), 6.41 (d, J=1.2 Hz, 1H), 7.98 (d, J=1.2 Hz, 1H).

Example 25

6-Bromo-1,3-dihydrofuro[3,4-c]pyridine

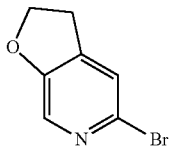

A mixture of copper(II) bromide (92 mg, 0.44 mmol), nitrous acid tert-butyl (85 mg, 0.82 mmol), and tetrahydrofuran (1 mL) was stirred at 50° C. A suspension of 1,3-dihydrofuro[3,4-c]pyridin-6-amine according to Example 24 (28 mg, 0.21 mmol) in tetrahydrofuran (0.5 mL) was added dropwise to the mixture, and the resulting mixture was stirred for 1 hour and 30 minutes. The reaction mixture was cooled to room temperature, and then concentrated under reduced pressure. The residue was purified by filtration through NH-silica gel (ethyl acetate:heptane=2:1), and then the obtained roughly purified product was separated and purified by preparative thin-layer NH-silica gel column chromatography (ethyl acetate:heptane=1:3) to obtain the title compound (12 mg, 30% yield).

¹H-NMR Spectrum (400 MHz, CDCl₃) δ (ppm): 5.07 (s, 2H), 5.10 (s, 2H), 7.41 (s, 1H), 8.29 (s, 1H).

Example 26

5,7-Dihydrofuro[3,4-d]pyrimidin-2-amine

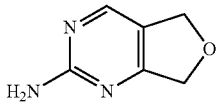

A mixture of tributyl({[(tributylstannyl)methoxy]methyl})stannane according to Production Example 1-2 (600 mg, 0.96 mmol), 1,4-dioxane (10 mL), 5-bromo-4-chloropyrimidin-2-amine (200 mg, 0.96 mmol), tris(dibenzylideneacetone)dipalladium (88 mg, 0.096 mmol), and X-Phos (100 mg, 0.21 mmol) was stirred at 130° C. for 8 hours under microwave irradiation. The mixture was cooled to room temperature, and then the insoluble matter was filtered off. The filtrate was washed with ethyl acetate, and then the filtrate was concentrated. The residue was separated and purified by silica gel column chromatography (heptane:ethyl acetate:methanol=1:1:0-0:9:1, gradient) to obtain the title compound (30 mg, 23% yield).

¹H-NMR Spectrum (500 MHz, CDCl₃) δ (ppm): 4.85 (s, 2H), 5.01-5.12 (m, 2H), 5.05 (s, 2H), 8.18 (s, 1H).

Example 27

2-Chloro-5,7-dihydrofuro[3,4-d]pyrimidine

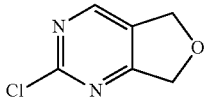

A suspension of 5,7-dihydrofuro[3,4-d]pyrimidin-2-amine according to Example 26 (25 mg, 0.18 mmol) in tetrahydrofuran (0.8 mL) was added dropwise to a mixture of copper(II) chloride (50 mg, 0.37 mmol), nitrous acid t-butyl (38 mg, 0.37 mmol), and tetrahydrofuran (0.5 mL) at 65° C., and the resulting mixture was stirred for 2 hours and 30 minutes. The insoluble matter was filtered off, the resultant was washed with ethyl acetate, and then the filtrate was concentrated by using a nitrogen blowing device. The residue was separated and purified by silica gel column chromatography (heptane:ethyl acetate=1:0-2:3, gradient) to obtain the title compound (13 mg, 46% yield).

¹H-NMR Spectrum (500 MHz, CDCl₃) δ (ppm): 5.02 (s, 2H), 5.18 (s, 2H), 8.50 (s, 1H).

Example 28

2-(Tributylstannyl)-5,7-dihydrofuro[3,4-d]pyrimidine

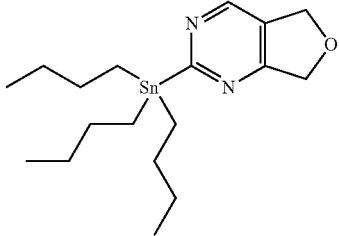 [SMILES: CCC[CH2][Sn]([CH2]CCC)([CH2]CCC)[c]1ncc2c(n1)COC2]

A mixture of 2-chloro-5,7-dihydrofuro[3,4-d]pyrimidine according to Example 27 (12 mg, 0.077 mmol), tetrakis(triphenylphosphine)palladium(0) (20 mg, 0.017 mmol), hexa-(n-butyl)ditin (200 μL, 0.40 mmol), and xylene (0.4 mL) was stirred at 135° C. for 4 hours. The reaction mixture was cooled to room temperature, and then a 1 N aqueous solution of potassium fluoride 1 mL was added to the reaction mixture, and the resulting mixture was stirred for 1 hour. The insoluble matter was filtered off, and the resultant was washed with ethyl acetate. The organic layer in the filtrate was separated, washed with a saturated saline solution, dried over anhydrous sodium sulfate, and then concentrated. The residue was separated and purified by silica gel column chromatography (heptane:ethyl acetate=1:0-4:1, gradient) to obtain the title compound (10 mg, 32% yield).

¹H-NMR Spectrum (500 MHz, CDCl₃) δ (ppm): 0.88 (t, J=7.3 Hz, 9H), 1.11-1.25 (m, 6H), 1.25-1.40 (m, 6H), 1.53-1.64 (m, 6H), 5.02 (s, 2H), 5.16 (s, 2H), 8.60 (s, 1H).

Example 29

2-Chloro-5,7-dihydrofuro[3,4-b]pyrazine

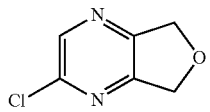

5,7-Dihydrofuro[3,4-b]pyrazin-2-amine according to Example 6 (38 mg, 0.28 mmol) was added to a mixture of copper(II) chloride (150 mg, 1.12 mmol), tert-butyl nitrite (60 mg, 0.58 mmol), and tetrahydrofuran (3 mL) at 65° C. in portions, and the resulting mixture was stirred for 2 hours. The resulting mixture was cooled to room temperature, and then poured onto silica gel. The mixture was concentrated, and then dried under reduced pressure. The obtained solid was separated and purified by silica gel column chromatography (heptane:ethyl acetate=1:0-1:1, gradient) to obtain the title compound (16 mg, 37% yield).

$^1$H-NMR Spectrum (400 MHz, CDCl$_3$) δ (ppm): 5.11 (s, 2H), 5.12 (s, 2H), 8.45 (s, 1H).

Example 30

2-(Tributylstannyl)-5,7-dihydrofuro[3,4-b]pyrazine

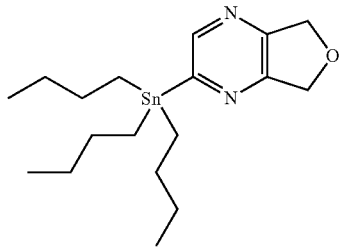 [SMILES: CCC[CH2][Sn]([CH2]CCC)([CH2]CCC)[c]1cnc2c(n1)COC2]

A mixture of 2-chloro-5,7-dihydrofuro[3,4-b]pyrazine according to Example 29 (12 mg, 0.077 mmol), tetrakis(triphenylphosphine)palladium(0) (20 mg, 0.017 mmol), hexa-(n-butyl)ditin (200 μL, 0.40 mmol), and xylene (0.4 mL) was stirred at 135° C. for 3 hours and 30 minutes. The reaction mixture was cooled to room temperature, and then a 1 N aqueous solution of potassium fluoride 1 mL was added thereto, and the resulting mixture was stirred for 1 hour. The insoluble matter was filtered off, and the resultant was washed with ethyl acetate. The organic layer in the filtrate was transferred to another test tube, and concentrated by using a nitrogen blowing device. The residue was separated and purified by silica gel column chromatography (heptane:ethyl acetate=1:0-4:1, gradient) twice to obtain the title compound (5 mg, 16% yield).

$^1$H-NMR Spectrum (400 MHz, CDCl$_3$) δ (ppm): 0.86 (t, J=7.2 Hz, 9H), 1.10-1.18 (m, 6H), 1.22-1.36 (m, 6H), 1.50-1.60 (m, 6H), 5.07 (s, 2H), 5.12 (s, 2H), 8.34 (s, 1H).

Example 31

Potassium (5,7-dihydrofuro[3,4-b]pyridin-3-yl)trifluoro borate

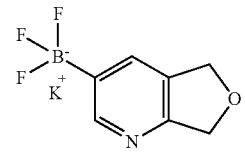

To a mixture of 3-(4,4,5,5-tetramethyl-1,3,2-dioxaborolan-2-yl)-5,7-dihydrofuro[3,4-b]pyridine according to Example 20 (9 mg, 0.036 mmol), potassium hydrogen fluoride (9 mg, 0.12 mmol), and methanol (0.9 mL), water (0.45 mL, 25 mmol) was added dropwise, and the resulting mixture was stirred at room temperature for 2 hours and 15 minutes. Potassium hydrogen fluoride (9 mg, 0.12 mmol) was added to the obtained mixture, and the resulting mixture was stirred at room temperature for 30 minutes. The reaction mixture was concentrated, and toluene was added to the obtained residue to concentrate the resulting mixture again. Ether was added to the solid residue, and the liquid phase was eliminated by decantation. This operation was repeated 3 times, and the remaining solid was dried under reduced pressure. A mixed liquid of 10% methanol-acetonitrile was added to the obtained solid, the insoluble matter was filtered off, and the resultant was washed with a mixed liquid of 10% methanol-acetonitrile. The filtrate was concentrated, and then dried under reduced pressure to obtain the title compound (8 mg, 97% yield).

$^1$H-NMR Spectrum (400 MHz, CDCl$_3$) δ (ppm): 4.95 (s, 2H), 5.10 (s, 2H), 7.78 (s, 1H), 8.43 (s, 1H).

Example 32

2-Chloro-5,7-dihydrofuro[3,4-b]pyridine

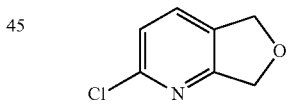

A solution of copper(II) chloride (99 mg, 0.73 mmol) and nitrous acid tert-butyl (88 μL, 0.73 mmol) in tetrahydrofuran (2.0 mL) was heated to 50° C., and a solution of 5,7-dihydrofuro[3,4-b]pyridin-2-amine according to Example 7 (50 mg, 0.37 mmol) in tetrahydrofuran (1.0 mL) was added dropwise to the resulting solution over more than 5 minutes. The reaction solution was stirred at 50° C. for 1 hour, it was confirmed by using thin-layer chromatography that the starting material had vanished, and then the reaction solution was cooled to room temperature. Ethyl acetate was added to the reaction solution, the resulting mixture was filtered through Celite and then the filtrate was concentrated under reduced pressure. The residue was separated and purified by silica gel column chromatography to obtain the title compound (13 mg, 22% yield).

$^1$H-NMR Spectrum (400 MHz, CDCl$_3$) δ (ppm): 5.04 (t, J=1.8 Hz, 2H), 5.15 (dd, J=2.0 Hz, 2H), 7.23 (d, J=8.1 Hz, 1H), 7.52 (d, J=8.1 Hz, 1H).

Example 33

2-Bromo-5,7-dihydrofuro[3,4-b]pyridine

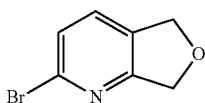

A solution of copper(II) bromide (260 mg, 1.2 mmol) and nitrous acid tert-butyl (140 μL, 1.2 mmol) in tetrahydrofuran (1.5 mL) was heated to 50° C., and a solution of 5,7-dihydrofuro[3,4-b]pyridin-2-amine according to Example 7 (81 mg, 0.59 mmol) in tetrahydrofuran (1.0 mL) was added dropwise to the resulting solution over more than 5 minutes. The reaction solution was stirred at 50° C. for 1 hour, it was confirmed by using thin-layer chromatography that the starting material had vanished, and then the reaction solution was cooled to room temperature. Ethyl acetate was added to the reaction solution, the resulting mixture was filtered through Celite, and then the filtrate was concentrated under reduced pressure. The residue was separated and purified by silica gel column chromatography to obtain the title compound (17 mg, 14% yield).

$^1$H-NMR Spectrum (400 MHz, CDCl$_3$) δ (ppm): 5.04 (d, J=1.6 Hz, 2H), 5.12 (d, J=1.2 Hz, 2H), 7.35-7.49 (m, 2H).

Example 34

2-(Tributylstannyl)-5,7-dihydrofuro[3,4-b]pyridine

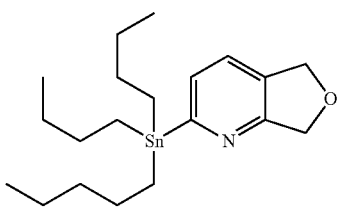 [SMILES: CCCC[CH2][Sn]([CH2]CCC)([CH2]CCC)[c]1ccc2c(n1)COC2]

A solution of 2-bromo-5,7-dihydrofuro[3,4-b]pyridine according to Example 33 (9.8 mg, 0.049 mmol), tetrakis(triphenylphosphine)palladium(0) (11 mg, 9.8 μmol), and hexa-(n-butyl)ditin (120 μL, 0.25 mmol) in xylene (350 μL) was heated to 135° C., and the resulting mixture was stirred for 4 hours. The reaction solution was cooled to room temperature, ethyl acetate was added to the reaction solution, the resulting mixture was filtered through Celite, and then the filtrate was concentrated under reduced pressure. The residue was separated and purified by silica gel column chromatography to obtain the title compound (5.8 mg, 29% yield).

$^1$H-NMR Spectrum (500 MHz, CDCl$_3$) δ (ppm): 0.80-1.03 (m, 9H), 1.06-1.23 (m, 6H), 1.26-1.52 (m, 6H), 1.52-1.63 (m, 6H), 5.09 (s, 2H), 5.14 (br s, 2H), 7.23-7.30 (m, 1H), 7.37 (d, J=7.3 Hz, 1H).

Example 35

1-Chloro-5,7-dihydrofuro[3,4-d]pyridazine

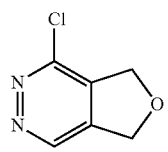

1,2,5,7-Tetrahydrofuro[3,4-d]pyridazin-1-one according to Example 1 (100 mg, 0.72 mmol) and thionyl chloride (1.0 mL) were mixed, and the mixture was heated to 90° C. and stirred for 4 hours. The reaction solution was cooled to room temperature, and then iced water was carefully added thereto in an ice bath. After the reaction settled, the resulting mixture was neutralized with a 1 N aqueous solution of sodium hydroxide and extraction with dichloromethane was carried out three times. The organic layers were combined together, dried over anhydrous magnesium sulfate, and then filtered through Celite. The filtrate was concentrated under reduced pressure, and then the residue was separated and purified by silica gel column chromatography to obtain the title compound (20 mg, 18% yield).

$^1$H-NMR Spectrum (400 MHz, CDCl$_3$) δ (ppm): 5.20 (br s, 2H), 5.28 (br s, 2H), 9.17 (br s, 1H).

Example 36

4-Chloro-5,7-dihydrofuro[3,4-d]pyrimidine

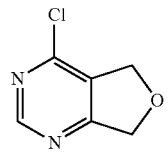

A solution of copper(II) chloride (82 mg, 0.61 mmol) and nitrous acid tert-butyl (73 μL, 0.61 mmol) in tetrahydrofuran (2.0 mL) was heated to 65° C., and a solution of 4-amino-5,7-dihydrofuro[3,4-d]pyrimidine according to Example 14 (42 mg, 0.31 mmol) in tetrahydrofuran (1.0 mL) was added dropwise to the resulting solution over more than 5 minutes. The reaction solution was stirred at 65° C. for 1 hour, it was confirmed by using thin-layer chromatography that the starting material had vanished, and then the reaction solution was cooled to room temperature. Ethyl acetate was added to the reaction solution, the resulting mixture was filtered through Celite, and then the filtrate was concentrated under reduced pressure. The residue was separated and purified by silica gel column chromatography to obtain the title compound (1.4 mg, 2.9% yield).

$^1$H-NMR Spectrum (400 MHz, CDCl$_3$) δ (ppm): 5.15 (s, 2H), 5.23 (s, 2H), 8.94 (s, 1H).

Example 37

Ethyl 4,6-dihydrothieno[2,3-c]furan-2-carboxylate

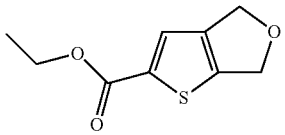

To a mixture of ethyl 4,5-dibromothiophene-2-carboxylate (100 mg, 0.32 mmol), tributyl{[(tributylstannyl)methoxy]methyl}stannane (200 mg, 0.32 mmol), and 1,4-dioxane (3.0 mL), tris(dibenzylideneacetone)dipalladium (29 mg, 0.032 mmol) and X-Phos (33 mg, 0.22 mmol) were added at room temperature under a nitrogen atmosphere. The reaction mixture was stirred at 130° C. for 8 hours under microwave irradiation. The reaction mixture was returned to room temperature, filtered through Celite, and then concentrated under reduced pressure. The residue was purified by column chromatography (ethyl acetate/heptane=7-15-25%) to obtain the title compound (28 mg, 44% yield).

$^1$H-NMR Spectrum (400 MHz, CDCl$_3$) δ (ppm): 1.38 (t, J=7.2 Hz, 3H), 4.35 (q, J=7.2 Hz, 2H), 4.96-4.97 (m, 2H), 5.09-5.11 (m, 2H), 7.53 (s, 1H).

Example 38

Methyl 1,3-dihydrofuro[3,4-c]pyridine-4-carboxylate

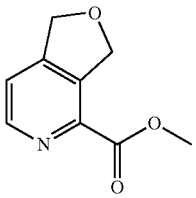

To a solution of 3,4-dichloropicolinic acid (1.0 g, 5.2 mmol) and N,N-dimethylformamide (0.10 mL, 1.3 mmol) in dichloromethane (15 mL), oxalyl chloride (0.90 mL, 10 mmol) was added dropwise at room temperature over 5 minutes. The resulting mixture was stirred at room temperature for 1 hour, and then methanol (2.5 mL) was added dropwise thereto. The resulting mixture was stirred for 1.5 hours, and then the solvent was distilled off under reduced pressure. Dichloromethane was added to the residue, and an azeotropic reaction was run twice to obtain a roughly purified product of 3,4-dichloropicolinic acid methyl ester (1.6 g).

Tributyl({[(tributylstannyl)methoxy]methyl})stannane according to Production Example 1-1 (300 mg, 0.49 mmol), tris(dibenzylideneacetone)dipalladium (44 mg, 0.049 mmol), X-Phos (51 mg, 0.11 mmol), and 1,4-dioxane (3 mL) were added to the obtained roughly purified product (100 mg), and the resulting mixture was stirred for 11 hours while being heated to reflux. The resulting mixture was cooled to room temperature, then a saturated aqueous solution of potassium fluoride (0.2 mL) was added, and the resulting mixture was stirred at room temperature for 1 hour. The resulting mixture was filtered through Celite and concentrated under reduced pressure. The residue was separated and purified by silica gel column chromatography (ethyl acetate:heptane=1:1) to obtain the title compound (16 mg, 28% yield).

$^1$H-NMR Spectrum (500 MHz, CDCl$_3$) δ (ppm): 4.02 (s, 3H), 5.15-5.17 (m, 2H), 5.43-5.46 (m, 2H), 7.41 (d, J=4.9 Hz, 1H), 8.67 (d, J=4.9 Hz, 1H).

Example 39

1,3-Dihydrofuro[3,4-c]pyridine-4-carboxylic acid

To a solution of methyl 1,3-dihydrofuro[3,4-c]pyridine-4-carboxylate according to Example 38 (180 mg, 1.0 mmol) in methanol (4 mL), a 2 N aqueous solution of sodium hydroxide (2 mL, 4 mmol) was added, and the resulting mixture was stirred at room temperature for 40 minutes. A 2 N hydrochloric acid (2 mL) was added to the reaction mixture, and then the solvent was distilled off under reduced pressure. The residue was subjected to reverse-phase silica gel column chromatography (acetonitrile-water-0.1% acetic acid), and the obtained fraction was concentrated to obtain a white solid. The obtained solid was suspended in a solution of acetonitrile:methanol=9:1, ground by sonication, and the solid was filtered off. The filtrate was concentrated to obtain the title compound (62 mg, 37% yield).

$^1$H-NMR Spectrum (400 MHz, DMSO-d$_6$) δ (ppm): 5.05-5.08 (m, 2H), 5.23-5.26 (m, 2H), 7.63 (d, J=4.7 Hz, 1H), 8.60 (d, J=4.7 Hz, 1H).

Example 40 tert-Butyl(1,3-dihydrofuro[3,4-c]pyridin-4-yl)carbamate

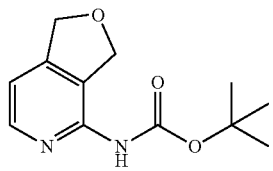 [SMILES: CC(C)(C)OC(=O)Nc1nccc2c1COC2]

To a solution of 1,3-dihydrofuro[3,4-c]pyridine-4-carboxylic acid according to Example 39 (30 mg, 0.18 mmol) in tert-butanol (2 mL), diphenylphosphoryl azide (0.040 mL, 0.19 mmol) and triethylamine (0.030 mL, 0.22 mmol) were sequentially added, and the resulting mixture was stirred for 10 hours and 30 minutes while being heated to reflux. The resulting mixture was cooled to room temperature, and then the solvent was distilled off under reduced pressure. The residue was separated and purified by silica gel column chromatography (ethyl acetate:heptane=3:2) to obtain the title compound (22 mg, 52% yield).

$^1$H-NMR Spectrum (400 MHz, CDCl$_3$) δ (ppm): 1.51 (s, 9H), 5.06-5.09 (m, 2H), 5.17-5.21 (m, 2H), 6.99 (d, J=4.7 Hz, 1H), 7.75 (br s, 1H), 8.21 (d, J=4.7 Hz, 1H).

Example 41

1,3-Dihydrofuro[3,4-c]pyridin-4-amine

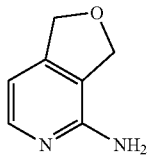

To a solution of tert-butyl(1,3-dihydrofuro[3,4-c]pyridin-4-yl)carbamate according to Example 40 (22 mg, 0.094 mmol) in dichloromethane (1 mL), trifluoroacetic acid (0.5 mL) was added, and the resulting mixture was stirred at room temperature for 30 minutes. The resulting mixture was diluted with toluene, and the reaction mixture was concentrated under reduced pressure. The residue was separated and purified by NH-silica gel column chromatography (ethyl acetate:methanol=4:1) to obtain the title compound (6.2 mg, 48% yield).

$^1$H-NMR Spectrum (500 MHz, CD$_3$OD) δ (ppm): 4.92-4.95 (m, 2H), 4.99-5.03 (m, 2H), 6.61 (d, J=5.4 Hz, 1H), 7.82 (d, J=5.4 Hz, 1H).

Comparative Example 3

2-Amino-N-(4-(benzyloxy)benzyl)-5,6-dimethylnicotinamide

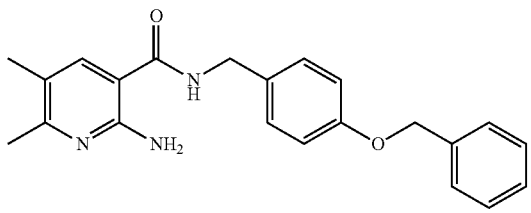 [SMILES: Cc1cc(C(=O)NCc2ccc(OCc3ccccc3)cc2)c(N)nc1C]

2-Amino-N-(4-(benzyloxy)benzyl)-5-bromo-6-chloronicotinamide according to Production Example 42-2 (50 mg, 0.11 mmol), tetramethyltin (60 mg, 0.34 mmol), tris(dibenzylideneacetone)dipalladium (10 mg, 0.011 mmol), X-Phos (21 mg, 0.045 mmol), and N-methylpyrrolidone (1.5 mL) were mixed, and the resulting mixture was stirred at 130° C. for 4 hours under microwave irradiation. The resulting mixture was cooled to room temperature, an aqueous solution of potassium fluoride was added thereto, and then the resulting mixture was stirred at room temperature overnight. The reaction solution was filtered through Celite, and ethyl acetate and water were added to the filtrate for separation. The obtained water layer was extracted with ethyl acetate. The obtained organic layers were combined together, washed sequentially with water and a saturated saline solution, and then dried over anhydrous sodium sulfate. The desiccant was filtered off, and the obtained filtrate was concentrated under reduced pressure. The residue was roughly purified by silica gel column chromatography (ethyl acetate:heptane=35:65-65:35, gradient), and then the obtained roughly purified product was roughly purified again by silica gel column chromatography (ethyl acetate:heptane=46:54-67:33, gradient). The obtained roughly purified product was purified by NH-silica gel column chromatography (ethyl acetate:heptane=25:75-60:40, gradient) to obtain the title compound (21 mg, 53% yield).

$^1$H-NMR Spectrum (400 MHz, CDCl$_3$) δ (ppm): 2.14 (br s, 3H), 2.35 (br s, 3H), 4.53 (br s, 2H), 5.08 (br s, 2H), 6.18 (br s, 3H), 6.93-7.02 (m, 2H), 7.24-7.50 (m, 8H).

Reference Example 3

2-Amino-N-(4-(benzyloxy)benzyl-5,7-dihydrofuro[3,4-b]pyridine-3-carboxamide

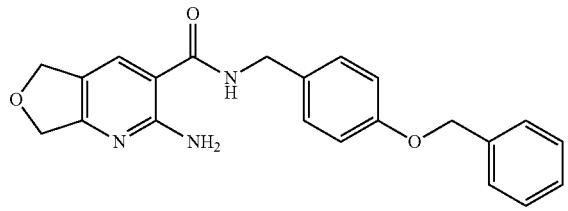 [SMILES: Nc1nc2c(cc1C(=O)NCc1ccc(OCc3ccccc3)cc1)COC2]

2-Amino-N-(4-(benzyloxy)benzyl)-5-bromo-6-chloronicotinamide according to Production Example 42-1 (50 mg, 0.11 mmol) tributyl({[(tributylstannyl)methoxy]methyl}) stannane according to Production Example 1-2 (70 mg, 0.11 mmol), tris(dibenzylideneacetone)dipalladium (10 mg, 0.011 mmol), X-Phos (21 mg, 0.045 mmol), and N-methylpyrrolidone (3 mL) were stirred at 130° C. for 4 hours under microwave irradiation. The resulting mixture was cooled to room temperature, an aqueous solution of potassium fluoride was added thereto, and then the resulting mixture was stirred at room temperature overnight. The reaction solution was filtered through Celite, and ethyl acetate and water were added to the filtrate for separation. The obtained water layer was extracted with ethyl acetate. The obtained organic layers were combined together, washed sequentially with water and a saturated saline solution, and then dried over anhydrous sodium sulfate. The desiccant was filtered off, and the obtained filtrate was concentrated under reduced pressure. The residue was roughly purified by silica gel column chromatography (ethyl acetate:heptane=40:60-75:25, gradient), and then the obtained roughly purified product was roughly purified again by NH-silica gel column chromatography (ethyl acetate:heptane=30:70-60:40, gradient). The obtained roughly purified product was separated and purified by preparative LCMS (mobile phase: acetonitrile/water, 0.1% acetic acid) to obtain the title compound (1.5 mg, 3.5% yield).

$^1$H-NMR Spectrum (400 MHz, CDCl$_3$) δ (ppm): 4.47-4.58 (m, 2H), 4.86-4.93 (m, 2H), 5.02 (br s, 2H), 5.05-5.11 (m, 2H), 6.16 (br s, 1H), 6.43 (br s, 2H), 6.92-7.02 (m, 2H), 7.23-7.50 (m, 8H).

Production Example 42-1

2-Amino-N-(4-(benzyloxy)benzyl)-6-chloronicotinamide

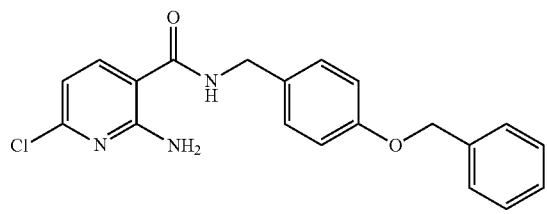 [SMILES: Nc1nc(Cl)ccc1C(=O)NCc1ccc(OCc2ccccc2)cc1]

To a solution of 2-amino-6-chloronicotinic acid (1.5 g, 8.7 mmol), (4-phenylmethoxyphenyl)methanamine hydrochloride (CAS No. 133100-92-2) (3.3 g, 13 mmol), benzotriazolyl-N-hydroxytrisdimethylaminophosphonium hexafluorophosphate (a BOP reagent) (5.8 g, 13 mmol) in N,N-dimethylformamide (100 mL), triethylamine (6.1 mL, 43 mmol) was added at 0° C., and the resulting mixture was stirred at room temperature for 19 hours. The reaction solution was concentrated under reduced pressure, and then ethyl acetate and water were added to the residue for separation. The obtained water layer was extracted with ethyl acetate. The obtained organic layers were combined together, washed with water and a saturated saline solution, and then dried over anhydrous magnesium sulfate. The desiccant was filtered off, and the obtained filtrate was concentrated under reduced pressure. The obtained residue was roughly purified by silica gel column chromatography (ethyl acetate:heptane=10:90-65:35, gradient). The obtained roughly purified product was suspended in ethyl acetate, and then processed by sonication and filtered. The obtained solid was washed with a small amount of ethyl acetate, and then dried under reduced pressure to obtain the title compound (2.3 g, 72% yield).

$^1$H-NMR Spectrum (400 MHz, CDCl$_3$) δ (ppm): 4.51 (d, J=5.5 Hz, 2H), 5.07 (s, 2H), 6.13 (br s, 1H), 6.50-6.65 (m, 3H), 6.96 (d, J=9.0 Hz, 2H), 7.23-7.45 (m, 7H), 7.50 (d, J=8.2 Hz, 1H).

Production Example 42-2

2-Amino-N-(4-(benzyloxy)benzyl)-5-bromo-6-chloronicotinamide

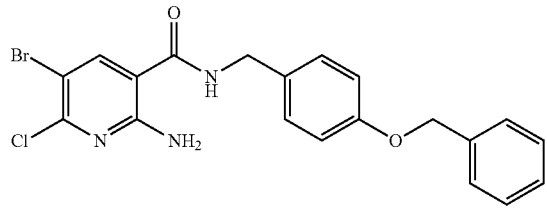 [SMILES: Nc1nc(Cl)c(Br)cc1C(=O)NCc1ccc(OCc2ccccc2)cc1]

To a solution of 2-amino-N-(4-(benzyloxy)benzyl)-6-chloronicotinamide according to Production Example 42-1 (1.0 g, 2.7 mmol), N,N-dimethylformamide (10 mL), and acetonitrile (40 mL), N-bromosuccinimide (NBS) (0.63 g, 3.5 mmol) was added at 0° C., and the resulting mixture was stirred at room temperature for 24 hours. N-bromosuccinimide (NBS) (0.13 g, 0.73 mmol) was added to this reaction liquid, and the resulting mixture was stirred at room temperature for 20 hours. The reaction solution was filtered, and the obtained solid was washed with a small amount of ethyl acetate and then dried under reduced pressure to obtain the title compound (600 mg, 50% yield). $^1$H-NMR Spectrum (400 MHz, DMSO-d$_6$) δ (ppm): 4.31-4.38 (m, 2H), 5.10 (br s, 2H), 6.93-7.02 (m, 2H), 7.20-7.28 (m, 2H), 7.29-7.48 (m, 5H), 7.66 (br s, 2H), 8.28-8.33 (m, 1H), 9.06 (br s, 1H).

[Evaluation on Solubility]

A 2.5 μL dimethyl sulfoxide solution (sample concentration: 10 mM) was added to the following test solution (0.25 mL), and was stirred with shaking at room temperature for about 15 minutes. The supernatant was then separated through vacuum filtration operation. A dimethyl sulfoxide solution (sample concentration: 100 μM) was used as a standard solution, and the sample concentration in the supernatant determined by an HPLC-UV method was defined as solubility.

Test solution: pH of 7, GIBCO™ (Dulbecco's phosphate-buffered saline, Invitrogen Corporation)

As shown in Table 1, it was verified that Reference Example 1 and Reference Example 2 had solubility higher than those of Comparative Example 1 and Comparative Example 2 with respect to solubility in the phosphate-buffered saline (pH: 7, GIBCO™).

TABLE 1

| | Comparative Example 1 | Reference Example 1 | Comparative Example 2 | Reference Example 2 |
|---|---|---|---|---|
| Solubility (μM) | 0.2 | 13.9 | 0.9 | 2.1 |

[Evaluation on Lipid Solubility]

(1) Method

A parameter of lipid solubility, i.e., a distribution ratio (D) of a 1-octanol to water (pH: 6.8) was determined with an ODS (silica gel having a surface modified with an octadecylsilyl group) column by the following method.

The mobile phase shown in Table 2 was added to sodium nitrate (to marker) and six standard substances having known partition coefficients shown in Table 2 to prepare mixed solutions each containing 5 μg/mL sodium nitrate and a 10 μg/mL or 10 μL/mL standard substance; these mixed solutions were used as standard solutions. The mobile phase shown in Table 3 was added to a sample, the concentration was adjusted to 0.1 mM to prepare a sample solution. HPLC analysis of the standard solutions and the sample solution was performed on the following conditions, and the retention times (t$_r$) of the standard substances and the sample were measured. From the retention factor (k$_{std}$) determined from the partition coefficient (log P) of the standard substance and Expression I, the regression coefficient (a) and the constant term (b) in Expression II were determined; using Expression III, the partition coefficient (log D) at a pH of 6.8 was calculated from the retention factor (k$_{smpt}$) of the sample; finally, the distribution ratio (D) of 1-octanol to water (pH: 6.8) was obtained.

TABLE 2

| Standard substance | Partition coefficient (logP) |
|---|---|
| Caffeine | −0.07 |
| Antipyrine | 0.38 |
| Carbamazepine | 2.45 |
| Ethylbenzene | 3.15 |
| n-Propylbenzene | 3.72 |
| n-Butylbenzene | 4.38 |

Reference: Exploring QSAR-Hydrophobic, and Steric Constants, Corwin Hansch, Albert Leo, and David Hoekman, ACS Professional Reference Book $$k=(t_r-t_0)/t_0 \quad \text{Expression I}$$

$$\log P = a \times \log k_{std} + b \quad \text{Expression II}$$

$$\log D = a \times \log k_{smp} + b \quad \text{Expression III}$$

(2) Measurement Conditions

Measurement was performed using the column and the mobile phase shown in Table 3 below

TABLE 3

| Column | Inertsil ODS-4 (3.0 mm I.D. × 150 mm, 5 μm) |
|---|---|
| Column temperature | 37 °C. |
| Mobile phase | 1/75 M phosphate-buffered saline/acetonitrile (60:40, v/v) |
| Flow rate | 0.8 mL/min |
| Detection | UV220 nm |
| Time for analysis | 15 min |

(3) Results

As shown in Table 4, it was verified that Comparative Example 1, Comparative Example 2, and Comparative Example 3 had values 3.5 to 13.2 times lower than those of Reference Example 1, Reference Example 2, and Reference Example 3, respectively with respect to the distribution ratio (D) as a parameter of lipid solubility.

TABLE 4

| | Comparative Example 1 | Reference Example 1 | Comparative Example 2 | Reference Example 2 | Comparative Example 3 | Reference Example 3 |
|---|---|---|---|---|---|---|
| Distribution ratio (D) | 1862 | 141 | 1820 | 525 | 2570 | 525 |

[Evaluation on Metabolic Stability of Human Liver Microsomes]

Evaluations on the metabolic stability of human liver microsomes prepared in Reference Examples 1 and 2 and Comparative Examples 1 and 2 produced using Examples were performed as follows.

A test compound was added to an enzyme solution (pooled human liver microsomes (0.2 mg/mL), 100 mM Kpi, containing 0.1 mM EDTA), and was incubated in the presence of a coenzyme for a predetermined time at 37° C. The final concentration of the test compound was 0.3 μM. As the coenzyme, an NADPH-generating system (solution in which 60 mM $MgCl_2$ solution containing 3.6 mM β-$NADP^+$, 90 mM glucose-6-phosphate, and 1 Unit/mL glucose-6-phosphate dehydrogenated enzyme was incubated at 37° C. for 5 minutes to generate NADPH) was used. After pre-incubation, part of the reaction solution was extracted; a double amount of a mixed solution of acetonitrile and methanol (7:3, containing 1.0 μM Propranolol as an internal standard substance) was added to terminate the reaction, and the concentration of the unchanged substance in the reaction solution was measured by LC-MS/MS. Based on the peak area of the unchanged substance obtained, the residual rate (%) of the unchanged substance was calculated wherein the residual rate at 0 min (incubation time) was 100%. Namely, the inclination of the straight line obtained when the value obtained by natural logarithmic conversion of the residual rate of the unchanged substance after a predetermined reaction time was plotted as the ordinate, and the reaction time was plotted as the abscissa was defined as an elimination rate constant (ke). Based on the obtained elimination rate constant ke, the hepatic intrinsic clearance of the test compound was calculated with the following expression:

Hepatic intrinsic clearance (mL/min/mg protein)=ke/(concentration of pooled human liver microsomes: mg protein/mL)

The residual rates (%) after 15 minutes, 30 minutes, and 60 minutes of the unchanged substance of the test compound and the hepatic intrinsic clearance values of the test compound are shown in Table 5 and Table 6. As shown in Table 5 and Table 6, it was verified that the clearances of human liver microsomes were improved in Reference Example 1, Reference Example 2, and Reference Example 3 compared to those of Comparative Example 1, Comparative Example 2, and Comparative Example 3, respectively.

TABLE 5

Metabolic stability of pooled human liver microsomes

| | | Comparative Example 1 | Reference Example 1 | Comparative Example 2 | Reference Example 2 |
|---|---|---|---|---|---|
| Residual rate of unchanged substance (%) | After 0 min | 100.0 | 100.0 | 100.0 | 100.0 |
| | After 15 min | 93.1 | 83.6 | 73.0 | 87.0 |

TABLE 5-continued

Metabolic stability of pooled human liver microsomes

| | | Comparative Example 1 | Reference Example 1 | Comparative Example 2 | Reference Example 2 |
|---|---|---|---|---|---|
| | After 30 min | 77.0 | 75.9 | 53.7 | 77.6 |
| | After 60 min | 56.2 | 61.4 | 30.9 | 65.4 |
| Hepatic intrinsic clearance (mL/min/mg protein) | | 0.050 | 0.039 | 0.098 | 0.035 |

TABLE 6

Metabolic stability of pooled human liver microsomes

| | | Comparative Example 3 | Reference Example 3 |
|---|---|---|---|
| Residual rate of unchanged substance (%) | After 0 min | 100.0 | 100.0 |
| | After 15 min | 65.0 | 78.0 |
| | After 30 min | — | — |
| | After 60 min | — | — |
| Hepatic intrinsic clearance (mL/min/mg protein) | | 0.150 | 0.082 |

[Pharmacological Test]

The anticandidal activity of Reference Examples 1, 2, and 3 and Comparative Examples 1, 2, and 3 produced using Examples and amphotericin B was measured as follows.

(1) Preparation of Bacterial Suspension

C. albicans CAF2-1 strains were subjected to static culture in a Sabouraud dextrose liquid culture medium (SDB) at 30° C. for 48 hours; and the bacterial suspension was diluted with an RPMI1640 culture medium to prepare a $1.2 \times 10^3$ cells/mL bacterial suspension.

(2) Preparation of Plates of Diluted Drugs

The diluted solutions of eight test compounds in plates (A to H) were prepared using a U-bottomed 96-well plate. 10 µL of a dimethyl sulfoxide solution was poured into columns 2 to 12 of the individual plates. The weighed test compounds were separately dissolved in dimethyl sulfoxide to prepare 2.5 mg/mL solutions; then, these solutions (20 µL) were placed in column 1 of the prepared plates, and were subjected to two-fold serial dilution in 12 steps on the plates (10 µL of solution+10 µL of dimethyl sulfoxide solution). The diluted solutions of the test compounds each were placed in a flat-bottomed 96-well plate for MIC measurement in an amount of 1 µL to prepare plates of the diluted test compound.

(3) Inoculation and Cultivation of Bacterial Suspension

The bacterial suspension prepared in (1) (99 µL/well) was inoculated into the flat-bottomed 96-well plate containing the diluted solutions of the test compounds (1 µL/well) prepared in (2), and was subjected to static culture at 35° C. for 42 to 48 hours under an aerobic condition.

(4) Measurement of MIC

The minimal concentration visually determined, at which the proliferation of bacteria was evidently reduced compared to that of control, was defined as a minimal inhibitory concentration (MIC).

As shown in Table 7, it was verified that Comparative Example 1, Reference Example 1, Comparative Example 2, Reference Example 2, Comparative Example 3, and Reference Example 3 all had strong anticandidal activity equal to that of amphotericin B.

TABLE 7

| | Anticandidal activity (MIC, µg/mL) |
|---|---|
| Comparative Example 1 | 0.13 |
| Reference Example 1 | 0.25 |
| Comparative Example 2 | 0.063 |
| Reference Example 2 | 0.50 |
| Comparative Example 3 | 0.13 |
| Reference Example 3 | 2.0 |
| Amphotericin B | 1.6 |

The invention claimed is:

1. A compound represented by formula (I) or a salt thereof:

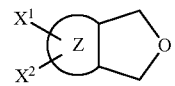

(I)

wherein the ring Z is a 6 membered heteroaromatic ring having one or two heteroatoms in the ring;

$X^1$ is —$B(OH)_2$, a boronate ester group, a cyclic boronate ester group, -$BF_3M_{n1}$ wherein n1 is 0 or 1 and M is an alkali metal, —$Sn(R^{12})(R^{13})(R^{14})$ wherein $R^{12}$, $R^{13}$, and $R^{14}$ are the same or different and are a $C_{1-6}$ alkyl group, or -L wherein L is a halogen atom, a methanesulfonyloxy group, a p-toluenesulfonyloxy group, or a trifluoromethanesulfonyloxy group; and $X^2$ is a hydrogen atom or —$CO_2R^{18}$ wherein $R^{18}$ is a hydrogen atom, a $C_{1-6}$ alkyl group, or a protecting group for a carboxy group.

2. The compound or the salt thereof according to claim 1, wherein the compound or the salt thereof is a compound represented by formula (III) or a salt thereof:

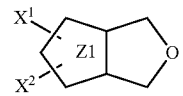

(II)

wherein the ring Z2 is a 6-membered heteroaromatic ring having one or two heteroatoms in the ring; and $X^1$ and $X^2$ are the same as defined as in claim 1.

3. The compound represented by formula (III) or the salt thereof according to claim 2, wherein the ring Z2 is a pyridine ring, a pyrazine ring, a pyrimidine ring, or a pyridazine ring.

4. The compound or the salt thereof according to claim 2, wherein the fused ring consisting of the ring Z2 and the adjacent ring is a furo[3,4-b]pyridine ring, a furo[3,4-c]pyridine ring, a furo[3,4-b]pyrazine ring, a furo[3,4-d]pyrimidine ring, a furo[3,4-c]pyridazine ring, or a furo[3,4-d]pyridazine ring.

5. The compound or the salt thereof according to claim 1, wherein the boronate ester group is a substituent represented by formula (Y-1) and the cyclic boronate ester group is a substituent represented by formulae (Y-2) to (Y-13)

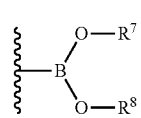

(Y-1)

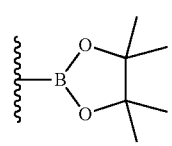

(Y-2)

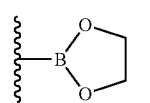

(Y-3)

(Y-4) 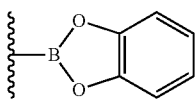

(Y-5) 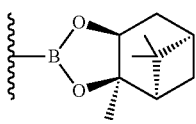

(Y-6) 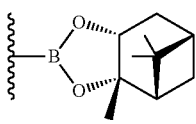

(Y-7) 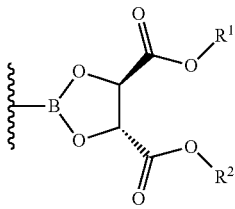

(Y-8) 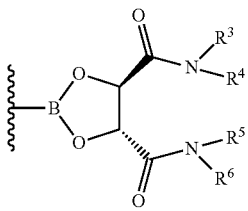

(Y-9) 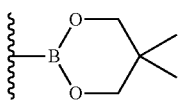

(Y-10) 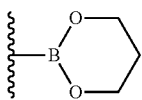

(Y-11) 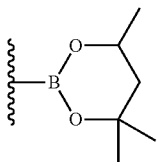

(Y-12) 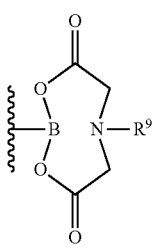

(Y-13) 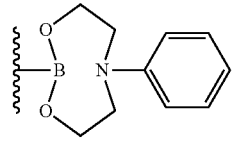

wherein $R^1$ to $R^9$ are the same or different and are a $C_{1-6}$ alkyl group.

6. The compound or the salt thereof according to claim 1, wherein the compound or the salt thereof is
1-bromo-5,7-dihydrofuro[3,4-d]pyridazine,
3-chloro-5,7-dihydrofuro[3,4-b]pyridine,
3-(4,4,5,5-tetramethyl-1,3,2-dioxaborolan-2-yl)-5,7-dihydrofuro[3,4-b]pyridine,
3-(tributylstannyl)-5,7-dihydrofuro[3,4-b]pyridine,
6-bromo-1,3-dihydrofuro[3,4-c]pyridine,
2-chloro-5,7-dihydrofuro[3,4-d]pyrimidine,
2-(tributylstannyl)-5,7-dihydrofuro[3,4-d]pyrimidine,
2-chloro-5,7-dihydrofuro[3,4-b]pyrazine,
2-(tributylstannyl)-5,7-dihydrofuro[3,4-b]pyrazine,
potassium (5,7-dihydrofuro[3,4-b]pyridin-3-yl)trifluoroborate,
2-chloro-5,7-dihydrofuro[3,4-b]pyridine,
2-bromo-5,7-dihydrofuro[3,4-b]pyridine,
2-(tributylstannyl)-5,7-dihydrofuro[3,4-b]pyridine,
1-chloro-5,7-dihydrofuro[3,4-d]pyridazine, or
4-chloro-5,7-dihydrofuro[3,4-d]pyrimidine.

7. A method of producing a compound represented by formula (I) or salt thereof according to claim 1:

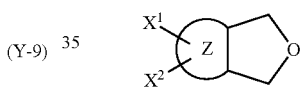

(I)

the method comprising reacting a compound represented by formula (IV):

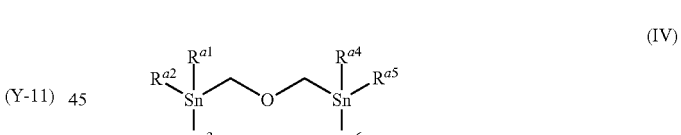

(IV)

wherein $R^{a1}$ to $R^{a6}$ are the same or different and are a $C_{1-6}$ alkyl group;
with a compound represented by formula (V):

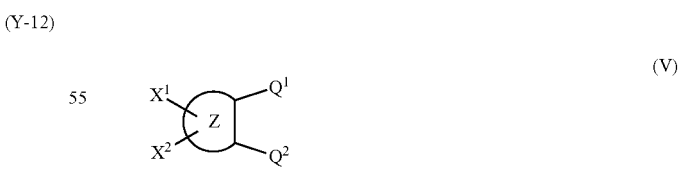

(V)

wherein $Q^1$ and $Q^2$ are each a leaving group, to form the compound represented by formula (I) or salt thereof.

* * * * *